United States Patent
Markus et al.

(10) Patent No.: US 9,655,359 B2
(45) Date of Patent: May 23, 2017

(54) SOLID CORE MICROCAPSULAR COMPOSITIONS AND USES THEREOF

(75) Inventors: Arie Markus, Beer-Sheva (IL); Charles Linder, Rehovot (IL); Pnina Strongin, Beer Sheva (IL)

(73) Assignee: BOTANOCAP LTD., Ashkelon (IL)

( * ) Notice: Subject to any disclaimer, the term of this patent is extended or adjusted under 35 U.S.C. 154(b) by 567 days.

(21) Appl. No.: 13/058,306

(22) PCT Filed: Aug. 11, 2009

(86) PCT No.: PCT/IL2009/000789
§ 371 (c)(1),
(2), (4) Date: Apr. 15, 2011

(87) PCT Pub. No.: WO2010/018576
PCT Pub. Date: Feb. 18, 2010

(65) Prior Publication Data
US 2011/0268780 A1    Nov. 3, 2011

Related U.S. Application Data

(60) Provisional application No. 61/087,755, filed on Aug. 11, 2008.

(51) Int. Cl.
| | |
|---|---|
| *A01N 25/34* | (2006.01) |
| *A01N 25/28* | (2006.01) |
| *A01N 65/00* | (2009.01) |
| *A01N 65/12* | (2009.01) |
| *A01N 65/22* | (2009.01) |
| *A23L 3/3463* | (2006.01) |
| *A23L 3/3472* | (2006.01) |
| *A61K 9/50* | (2006.01) |
| *A61K 35/60* | (2006.01) |
| *A61K 36/13* | (2006.01) |
| *A61K 36/53* | (2006.01) |
| *A61K 47/12* | (2006.01) |
| *C11D 3/50* | (2006.01) |
| *A01N 65/28* | (2009.01) |
| *A01N 65/06* | (2009.01) |
| *A01N 65/08* | (2009.01) |
| *A23P 10/30* | (2016.01) |
| *A23L 33/105* | (2016.01) |
| *A23L 33/135* | (2016.01) |

(52) U.S. Cl.
CPC ............ *A01N 25/28* (2013.01); *A01N 65/00* (2013.01); *A01N 65/06* (2013.01); *A01N 65/08* (2013.01); *A01N 65/12* (2013.01); *A01N 65/22* (2013.01); *A01N 65/28* (2013.01); *A23L 3/3463* (2013.01); *A23L 3/3472* (2013.01); *A23L 33/105* (2016.08); *A23L 33/135* (2016.08); *A23P 10/30* (2016.08); *A61K 9/5015* (2013.01); *A61K 9/5031* (2013.01); *A61K 35/60* (2013.01); *A61K 36/13* (2013.01); *A61K 36/53* (2013.01); *A61K 47/12* (2013.01); *C11D 3/505* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,130,450 A | 12/1978 | Bahder et al. | |
| 4,765,982 A | 8/1988 | Ronning et al. | |
| 5,178,872 A | 1/1993 | Ohtsubo et al. | |
| 5,229,122 A | 7/1993 | Chadwick et al. | |
| 5,741,521 A | 4/1998 | Knight et al. | |
| 5,885,600 A | 3/1999 | Blum et al. | |
| 6,015,773 A * | 1/2000 | Wysong et al. | 504/360 |
| 6,030,927 A | 2/2000 | Hodgkinson et al. | |
| 6,406,747 B1 * | 6/2002 | Biegelsen | B01J 13/04 427/213.32 |
| 6,565,860 B1 * | 5/2003 | Walker | 424/400 |
| 6,582,714 B1 | 6/2003 | Emmrich et al. | |
| 6,733,802 B1 * | 5/2004 | Moorty et al. | 424/761 |
| 7,846,463 B2 | 12/2010 | Johal | |
| 2004/0115280 A1 | 6/2004 | Podszun et al. | |
| 2006/0257441 A1 * | 11/2006 | Komai et al. | 424/405 |

FOREIGN PATENT DOCUMENTS

| | | | |
|---|---|---|---|
| EP | 0005302 A2 * | 2/1979 | |
| EP | 0005302 A2 | 11/1979 | |
| EP | 1702886 A1 | 9/2006 | |
| WO | 2004034791 A1 | 4/2004 | |
| WO | WO2004034791 * | 4/2004 | |
| WO | 2004098767 A1 | 11/2004 | |
| WO | WO2004098767 * | 11/2004 | |
| WO | 2006007756 A2 | 1/2006 | |
| WO | 2007094000 A2 | 8/2007 | |
| WO | 2007101917 A1 | 9/2007 | |

OTHER PUBLICATIONS

Aerosil (https://www.aerosil.com/product/aerosil/en/services/storage/pages/default.aspx; accessed Sep. 5, 2013).*
International Search Report and Written Opinion of the International Searching Authority Application No. PCT/IL2009/000789 Completed: Apr. 28, 2010; Mailing Date: Jul. 22, 2010 18 pages.

* cited by examiner

*Primary Examiner* — Devang Thakor
(74) *Attorney, Agent, or Firm* — Vorys, Sater, Seymour & Pease LLP

(57) ABSTRACT

Provided are microcapsules containing a solid core including at least one essential oil mixed with a porous solid material, where this solid core is coated by at least one layer of a polyurea film and/or a polyurethane film or an amphipathic shell composed of a multivalent salt form of at least one alkanoic acid. Further provided are compositions including these microcapsules, and uses thereof in a variety of agricultural and environmental applications.

25 Claims, No Drawings

SOLID CORE MICROCAPSULAR COMPOSITIONS AND USES THEREOF

This is a National Phase Application filed under 35 U.S.C. 371 as a national stage of PCT/IL2009/000789, filed on Aug. 11, 2009, an application claiming the benefit under 35 USC 119(e) of U.S. Provisional Application No. 61/087,755, filed on Aug. 11, 2008, the content of each of which is hereby incorporated by reference in its entirety.

BACKGROUND

Essential oils have been known for many years to have different desired properties, such as: antiseptic, disinfectant, antifungal, antibacterial etc. Consequently, essential oils have been used as natural products for a number of uses. Over the years, they have been replaced with less expensive but effective synthetic chemical agents, but—given the toxicity and environmental effects of these synthetic chemicals, there is a rising interest in using once more the natural essential oil agents. This objective necessitates the development of formulations that combine the desired properties of the natural essential oils while matching the efficacy of synthetic agents, at a low cost. This requires that the essential oils be formulated in cost effective controlled release rate carriers which release the essential oils at low but effective concentrations. It also requires that the entities carrying the essential oil be readily formulated into configurations for a given application.

WO 04/098767, by the inventors of the present application, discloses a process for the preparation of essential oil microcapsules by encapsulation of an essential oil through interfacial polymerization, whereby a polyurea and/or polyurethane film is formed around the liquid essential oil droplets. These microcapsules may be used as disinfectant products for the consumer market as hard-surface cleaners, laundry detergents and softeners, as pesticides, insect repellents, and as antiviral or antifungal agents.

WO 06/07756, also by the inventors of the present application, discloses agricultural formulations of essential oil microcapsules and uses thereof, which were also prepared by interfacial polymerization, and comprise a combination of a volatile essential oil and a non-volatile carrier. The microcapsules were a liquid core of essential oil optionally with additives and other active agents such as IGRs.

More recently, WO 07/094,000, also by the inventors of the present application, disclosed an aqueous ("green") method for preparing microcapsules comprising essential oils, by mixing at least one alkanoic acid with at least one essential oil; adding an aqueous basic solution to obtain a suspension; and mixing into this suspension an aqueous salt solution comprising a multivalent cation, which complexed with the acids groups of the alkanoic acids.

There is an going need of developing new formulations that would be better suited to address essential microcapsule characteristics needed by different industries.

For example, crops such as bananas, mangoes, peppers and carrots often become biologically contaminated by bacteria and/or fungi post-harvest. Contamination can be initiated pre-harvest (eg. by parasitic presence at the time of picking/harvesting), during harvesting (eg. where contaminants are introduced by mechanical harvesters or human intervention) and post-harvest (eg. where parasites and spore settle on post-harvested produce). Regardless of the time of contamination, it is necessary to treat harvested fruit, vegetables and plants prior to transportation and storage to eradicate any such contamination, as in fact is required by international authorities. Furthermore, post harvest treatment increases the shelf life of the crops and enables longer transportation and storage thereof.

So far, a variety of synthetic pesticides have been used to treat post-harvest crops, mostly by dipping (see for example U.S. Pat. No. 6,030,927) but there is an ever-increasing international concern over the residues of such pesticides on the treated fruits and vegetables.

Not only crops, but other foods, leather products, fur coats and products of paints and pastes formed of starch or cellulose, are prone to mold (a fungus that produces a superficial growth on various kinds of damp or decaying organic matter) or develop an increased growth of harmful microorganisms, mostly of bacteria. This considerably reduces the shelf life of these products.

Known methods to prevent such contamination of products are by seal-packing the product with an oxygen absorber to maintain a low oxygen concentration within the package, by sealing the product in an ethanol environment, or by using synthetic anti-fungal and anti-bacterial agents. Each of these methods is limited and has known disadvantages.

Preferably, it would have been desirable to find a treatment method which would use natural active ingredients, and that the actual formulation would be placed in close proximity to the product to be protected but would avoid direct contact with the treated crop or product.

For certain other applications, it is important to be able to control flying insects for several hours, in both indoors or outdoor environments. Traditionally, articles or devices that dispense insecticide vapors to control such insects in such settings require heating or burning a liquid or solid substrate to evaporate the active ingredients (for example, citronella candles and similar products). Alternative methods include employing passive evaporation of insect control active ingredients without the application of heat, but their application is quite limited: for example, U.S. Pat. No. 4,130,450 discloses an insecticide-impregnated, open, low-density web that provides an expanded surface that may be loaded with contact insecticides, preferably micro-encapsulated pyrethrum, that is then evaporated to repel insects, such as flies or mosquitoes. Whitcomb mentions that the web may be hung to permit vaporization of the active ingredient to combat flies. Similarly, U.S. Pat. No. 5,229,122 utilizes a mixture of micro-encapsulated and non-micro-encapsulated active ingredients, noting that any known pesticide may be used for the purpose, including pyrethrum or a pyrethroid equivalent. The preparation is used to coat surfaces, although it is also noted that the vapor phase of the pesticides may be valuable. U.S. Pat. No. 4,765,982 is an example of the use of micro-encapsulated active ingredients to achieve a sustained release insect control effect of pyrethroids, either synthetic or "natural". U.S. Pat. No. 6,582,714 discloses an insect control article which has a substrate that is impregnated with an active insect control ingredient that is available for passive evaporation.

However, in all of the above-described methods the release rate of the active ingredient is far from effective or optimum, which requires frequent repeated application of the essential oil products and since in many cases the active agent is also relatively costly to make or purchase, thereby increasing the cost of the essential oil products as compared to less expensive synthetic chemicals which however are often toxic and environmentally harmful.

U.S. Pat. No. 5,885,600 uses selective methods to remove certain essential oils from vegetable matter, followed by immediate protection from peroxidation, until the proper antioxidants are added. The resultant composition may then be formulated into many different items all used as insecticides, for example in veterinary use or in environmental applications.

It would be desirable to enhance the shelf life of such products and thereby extend their usability range.

Some water bodies contain undesirable zooplankton or one or more forms of harmful or undesirable insects. Thus, maintaining an acceptable water quality of water reservoirs, in particular water reservoirs that supply water for drinking and domestic consumptions, is another important application.

For example, one type of chironomids (Arthropoda: Insecta: Diptera: Chironomidae, otherwise known as bloodworms) are bottom feeder red mosquito larvae that live in water. The red larvae of this insect account for the red colour occasionally obtained in drinking water. This is only one example of the esthetic and pollution problems that Chironomids and zooplankton can cause to water bodies used as reservoirs for drinking and domestic water supplies. Furthermore, it should be noted that in order to effectively treat such chironomids and zooplankton, the formulation has to settle on the bottom of the water body or at specific depths within the water body, rather than float on the surface.

To date, there are no effective means that use non-toxic and environmentally safe agents for controlling chironomids and zooplankton. Yet further, there are no such formulations which are specifically directed at depth-residing undesirable insects or zooplankton.

For example, in U.S. Pat. No. 5,178,872 a pesticidal composition containing a microencapsulated organo-phosphorus or carbamate in a pyrethroid dispersion, is described which may also be effective against Chironomids, but does not provide any teachings on actual use against Chironomids, in particular as to the suitability of the formulation in settling on the bottom of the water body.

Another example, U.S. Pat. No. 5,741,521, discloses a biodegradable controlled release amylaceous material matrix of an agriculturally active agent such as insecticides, fungicides, fertilizers, plant growth regulants, etc. Two formulations G01S05 & G01S09 were evaluated in a bioassay trial against the eastern false wireworm. Formulation G01S905 was also evaluated in a field trial for the residual control of Chironomid larvae (bloodworms) in establishing rice crops. There is no mention of the use however of these formulations on water bodies nor is their any indication that the formulations when applied to the water will settle to the bottom to treat Chironomid and zooplankton larvae at that site.

DETAILED DESCRIPTION OF THE INVENTION

The present invention provides microcapsules containing a solid core comprising at least one essential oil mixed with a porous solid material.

The inventors have now developed a large variety of such microcapsules, by several alternative methods, and have demonstrated the wide applicability of these enveloped solid core microcapsules.

As explained in the Background section hereinabove, presently known non-encapsulated products based on essential oils are required to be applied often because of the volatility of the essential oil and in many cases are sensitive to oxidation properties that impair their efficacy in many applications. Encapsulation is therefore needed to minimize evaporation and reduce oxidation by the encapsulating envelope and/or by co-encapsulation of formulation with antioxidants. However, presently known encapsulated essential oils do not have the absorption and staying power to the surfaces they are applied to, and/or do not have the required sustained releasing characteristic required for a cost effective product, being either too fast or two slow, and/or not being released at a constant rate.

The solid core microcapsules of the present invention further overcome the limitations of known non-encapsulated oil formulations and show an increased stability and furtherrelease an effective dose at a constant virtually unchanging rate (termed zero order release) giving a longer duration of activity than the same quantity of non-encapsulated oil. Thus, the quantity of essential oil that is needed to obtain efficacy is decreased and production costs are lowered.

As shown in the examples below, a large number of microcapsules were prepared according to the embodiments of the present reaction.

These microcapsules had in all cases a solid core comprising either one or more essential oils, mixed with a porous solid material. This solid core was encapsulated by one or more layers of a film or a membrane, and optionally further coated by one or more fatty layers. This resulted in microcapsules containing a solid core, which have a controllable coating type and layer, this being one of the factors for predetermining the release rate of the essential oil(s). The choice, combination and ratios of the essential oil(s) and additional ingredients also help determine the release rates of the oils.

Thus, according to a first aspect of the invention, there are provided microcapsules containing a solid core comprising at least one essential oil mixed with a porous solid material, wherein said solid core is coated by at least one layer of polyurea film and/or polyurethane film, or an amphipathic shell composed of a multivalent salt form of at least one alkanoic acid. Preferably, the at least one essential oil is mixed into and on the porous solid material.

The term "microcapsules" as used herein refers to solid particles or droplets mixed with an absorbent, that are surrounded by a coating to give small capsules having a size ranging from 0.1 to 1000 microns in diameter. For many applications, the microcapsules of the present invention have a size ranging from 10 to 100 microns in diameter, and for yet several other applications, for example for applications requiring soil migration, sub-micron particles are preferred, namely from 0.1 micron to a micron.

In particular, the microcapsules of the present invention have a shape approaching elliptical or spherical, with a solid porous core impregnated with essential oils and other components or additives, such that this solid core is then encapsulated by one or more films, formed by either interfacial polymerization or by complexation of alkanoic acids with multivalent ions, and whereas these films are optionally further coated by a variety of fatty materials.

The microcapsules of the present invention further include microcapsules wherein additional components or additives are added outside of the solid core, and are therefore present between the solid core and one of the encapsulating coatings.

The term "solid core" refers to a solid porous material which has the essential oils, and optionally additional ingredients absorbed within (into it and/or on it).

Generally, the solid core matter appears as micron sized particles but may be in some cases submicron, namely from 0.1 micron to a micron. This may be important in, for example, drip irrigation applications where soil mobility is of importance.

The Term "essential oil" generally refers to those botanical oils that give the plants their characteristic odors, flavors, or other such properties.

"Botanical oils" are natural complex mixtures of oils made by plants. They are found in various parts of the plant body (in the seeds, flowers, bark, or leaves) and are also concentrated in certain special cells or groups of cells (glands). In general, they are complex mixtures that may be obtained from the plant in various ways, depending upon the nature of the part in which they are found. Such methods may for example be by compression, by distillation with steam, by dissolving the oils out (extraction) or absorbing them, and by pressure and maceration. The term also refers to oil mixtures prepared by enriching naturally obtained botanical oils with one or more specific component such as monoterpenes, diterpenes, triterpenes, tetraterpenes, sesquiterpenes, and other polyterpenes as well as organic alcohols, aldehydes ketones, acids and esters.

While the terms "essential oils" and "botanical oils" are used in different literary sources interchangeably, within the scope of the present invention the latter refers to a larger group of compounds that also includes lipids.

"Lipids" as referred to herein include the fatty acids, the glycerol-derived lipids (including the fats and oils and the phospholipids), the sphingosine-derived lipids (including the ceramides, cerebrosides, gangliosides, and sphingomyelins), the steroids and their derivatives, the terpenes and their derivatives, certain aromatic compounds, and longchain alcohols and waxes. The term also refers to lipoproteins (lipids conjugated with proteins or carbohydrates), to lipopolysaccharides and to vitamins such as fat-soluble vitamins.

In a preferred embodiment, the oils are selected from sesame oil, pyrethrum, glycerol-derived lipids or glycerol fatty acid derivatives.

Examples of preferable essential oils, include but are not limited to, cinnamon oil, cedar oil, clove oil, geranium oil, lemongrass oil, mint oil, sesame oil, thyme oil, turmeric oil, wintergreen oil, rosemary oil, anise oil, cardamom oil, chamomile oil, coriander oil, cumin oil, dill oil, mint oil, parsley oil, basil oil, camphor oil, citronella oil, eucalyptus oil, fennel oil, ginger oil, grapefruit oil, lemon oil, mandarin oil, orange oil, pine needle oil, pepper oil, rose oil, sweet orange oil, tangerine oil, tea tree oil, tea seed oil, lavender oil, caraway oil, garlic oil, peppermint oil, onion oil and spearmint oil. In one embodiment, the essential oil is a volatile oil. In another embodiment, the essential oils is selected amongst citronella oil, geranium oil, tea tree oil, lavender oil, clove pine oil, eucalyptus oil, thyme oil, oregano oil, and other spice plant essential oils, as well as combinations and mixtures thereof. In a preferred embodiment, the essential oil is an edible essential oil.

The encapsulated essential oil is chosen according to the desired properties of the microcapsule and/or its desired applications. The choice of suitable essential oils is well known to a person skilled in the art.

Optionally, In addition to essential oils the solid core may also contain adjuvants or agents which enhance the properties of the essential oils, for example another active botanical oil or lipid, which contains components to enhance the pesticidal, insecticidal, larvicidal or antimicrobial properties of the microcapsule.

For example, the microcapsules may comprise in addition to the essential oil repellents pesticides such as insect growth regulators (IGR), herbicides, insecticides, acaracides, fungicides, nematicides, ectoparasiticides, and/or herbicides either within the microcapsule or as part of the vehicle.

Preferably, said formulation may contain pesticides which are soluble in either said at least one encapsulated essential oil or in the non-volatile vehicle. Such pesticides may for example be carbamates, ureas, triazines, triazoles, uracils, organophosphates, morpholines, dinitroanilines, acylalaninies, pyrethroids, and organochlorines. Specific examples are carbofuran, azinphos-methyl, sulfentrazone, carfentrazone-ethyl, cypermethrin, cyromazine, beta-cyfluthrin, endosulfan, phosmet, chlorobromuron, chloroxuron, chlorotoluron, fluometuron, metobromuron, thiazafluoron, teflubenzuron, hexaflumuron, diflubenzuron, flufenoxuron, lufenuron, chlorfluazuron, novaluron. dimethachlor, metolachlor, pretilachlor, 2-chloro-n-(1-methyl-2-methoxyethyl)-acet-2,6-xylidide, alachlor, butachlor, propachlor, dimethenamid, bifenox, 4-(4-pentyn-1-yloxy)diphenylether, acifluorfen, oxyfluorfen, fluoroglycofen-ethyl, fomesafen, cis,trans-(+)-2-ethyl-5-(4-phenoxyphenoxymethyl)-1,3-dioxolane, fluazifop-butyl, haloxyfop-methyl, haloxyfop-(2-ethoxyethyl), fluorotopic, fenoxapropethyl, quizalofopethyl, propaquizafop, diclofop-methyl, butralin, ethalfluralin, fluchloralin, isopropalin, pendimethalin, profluralin, trifluralin. aclalanines furalaxyl, metalaxyl, benzoylprop ethyl, flamprop methyl, difenoconazole, etaconazol, propiconazole, 1,2-(2, 4-dichlorophenyl)-pent-1-yl-1h-1,2,4-triazole, triadimefon, dioxacarb, furathiocarb, aldicarb, benomyl, secbutylphenyl-methylcarbamate, etiofencarb, fenoxycarb, isoprocarb, propoxur, carbetamid, butylate, di-allat, eptc, molinate, thiobencarb, tri-allate, vemolate, piperophos, anilofos, butamifos, azamethiphos, chlorfenvinphos, dichlorvos, diazinon, methidathion, azinphos ethyl, azinphos methyl, chlorpyrifos, chlorthiofos, crotoxyphos, cyanophos, demeton, dialifos, dimethoate, disulfoton, etrimfos, famphur, flusulfothion, fluthion, fonofos, formothion, heptenophos, isofenphos, isoxathion, malathion, mephospholan, mevinphos, naled, oxydemeton methyl, oxydeprofos, parathion, phoxim, pyrimiphos methyl, profenofos, propaphos, propetamphos, prothiophos, quinalphos, sulprofos, phemephos, terbufos, triazophos, trichloronate, fenamipos, isazophos, s-benzyl-o,odiisopropylphosphorothioate, edinphos and pyrazophos.

In one preferred embodiment, the microcapsules contain green IGRs, which are IGRs of natural sources, such as, for example, Neem oils, and individual fractions extracted from these natural IGRs, such as azadirachtin derived from Neem oils.

Optionally, the formulations may also comprise additives such as adjuvants, adhesives, antioxidants, water-resistant agents, surfactants, steric barrier polymers which prevent microcapsule aggregation and gel-breaking agents, as part of the vehicle or within the microcapsule.

Non-limiting examples of specific additives are gamma-linolenic acids, citrus oils, such as orange oil, nutritional supplements such as Vitamin A, Vitamin E, Vitamin C, and Vitamin D, tocopherols, tocotrienols, phytosterols, Vitamin K, beta-carotene, marine oils, omega-3 fatty acids, CoQ10, lipid soluble derivatives of polar antioxidants, such as ascobyl fatty acid esters, plant extracts such as rosemary, sage and oregano oils, algal extracts, and synthetic antioxidants such as BHT, TBHQ, ethoxyquin, alkyl gallates and hydroquinones or natural antioxidants. Other non-limiting examples of preferred additives in addition to surfactants are steric barrier polymers, which help maintain particle separation. These steric barrier polymers may be selected, without limitation, from polyvinylpyrrolidone (PVP), polyvinyl alcohol (PVA) and poly(ethoxy)nonylphenol.

Often it is most convenient to bottle or can the suspension containing the encapsulated essential oil, in which case it may be desirable to add formulation adjuvants before storing to improve suspension stability and ease of application. These adjuvants may be selected amongst density balancing agents, surfactants, thickeners, biocides, dispersants, antifreeze agents, salts, and the like. Typically, the adjuvant is to be added at a concentration of from about 0.01% to about 30% by weight.

According to a specifically preferred embodiment of the present invention, all of the components of the microcapsules, including the active ingredients, the coating materials, the porous solid material and any other additives or adjuvants, as discussed hereinabove, are derived from natural sources, or fractions thereof. These microcapsules are then termed "green microcapsules" or "natural microcapsules" and are particularly important as food additives, in the treatment of drinking water, in the treatment of household products or crops, and in fact in every application where the use of synthetic compounds and active ingredients is to be minimized.

The term "porous solid material", otherwise known as nonvolatile solid vehicle, is a material used as an absbsorbent solid core of the microcapsules of the present invention, and may therefore be interchangeably referred to as the "absorbent" or as the "absorbing porous solid material".

The terms "absorbed", "absorbent or "absorption", as used herein, refer to permeation and/or solvation of a liquid, in this case the essential oil, in a solid, in this case the porous solid material. However, the term "absorbed" also includes solid essential oils absorbed into the solid porous material.

Examples of preferable porous solid materials, according to the present invention, include, but are not limited to, aerogels, as defined and exemplified hereinbelow, as well as other porous inorganic or organic absorbents. In some applications combinations of different particles of different densities is desired achieve a range of densities of microcapsules in certain applications such as water applications where treatment over a range of different water depths is required, for example.

The term "aerogel" refers to a class of structures rather than a specific material, whereas these structures are highly porous solids formed from a gel in which the liquid is replaced with a gas (e.g., air). A variety of different aerogel compositions are possible and may be inorganic, organic and combined organic-inorganic. They can be made from Silica (of which aerosol is one preferred type of this invention and in particular the Aerosils), Carbon aerogels, Alumina aerogels, Chalcogels (aerogel made of chalcogens, such as sulfur, selenium, and other elements).

Specific examples of aerogels include, but are not limited to, magnesium oxide, calcium oxide, zinc oxide, aluminium oxide, titanium oxide, silicon oxide, swelling clays, metal oxides, metal silicates, metal carbonates, metal phosphonates, metal sulfates, carbides, nitrides, urethanes, resorcinol formaldehydes, polyimide, polyacrylates, chitosan, polymethyl methacrylate, a member of the acrylate family of oligomers, trialkoxysilylterminated poly-dimethylsiloxane, polyurethane, polybuta-diane, polyoxyalkylene, a polyether, or combinations thereof.

Preferably, the aerogel is a silica selected from Aerosil, Cab-O-Sil, Syloid, Porasil, Lichrosorp, Aeroperl, Sunsil, Zeofree and Sopernat.

The term "at least one essential oil mixed with a porous solid material" refers to the mixture formed between the essential oil(s), optionally including additional additives, and the porous solid material.

Preferably, the essential oil(s) are absorbed within (into and/or on) the porous solid material. More preferably, the essential oil(s) are uniformly and evenly absorbed within the porous solid material.

The term "polyurea and/or polyurethane film", refers to a film prepared from the interfacial polymerization of di- or polyisocyante by water and/or polyhydroxy compounds and/or amines. Thus, the reaction of the di- or polyisocyante with water and amines forms polyureas. Similarly, and the reaction of the di- or polyisocyante with polyhydroxy compounds or/and water forms polyurethanes.

The encapsulating film may be predominately either polyurethane or polyureas or a combination of both polyurethane and polyurea encapsulating films. Multiple encapsulating layers may also be formed where for example one of the layers is a polyurethane and the other layer a polyurea.

It should be noted that the obtained polyurea and/or polyurethane film is a tough thin film having a permeability which is readily controlled by the conditions of the polymerization, the composition of the reactants and the catalysts. The resultant materials are non-toxic and ultimately biodegradable.

The term "film" refers to a thin, and preferably uniform, coating encapsulating the solid porous core containing the essential oils and the optional other ingredients and additives. In some cases the term "membrane" is used, to denote a film that has a specific permeability, or allows the selected passage of certain compounds through it. For example, the selected passage of the essential oils or other specific additives, out of the microcapsules.

The term "thin film" as used herein refers to a thickness of between about 0.5 nanometer to about 10 microns.

It is important to note that the term "film", as defined herein, also encompasses the kind of coating formed by complexation of the amphiphilic compounds (in this case the alkanoic acid) linking the essential oils present within the solid core through the hydrophobic side, and the multivalent cations through the hydrophilic side (having the ionic head). Thus, the term "amphipathic shell composed of a multivalent salt form of at least one alkanoic acid" is a type of film, as defined hereinabove.

The term "encapsulating" is used interchangeably with the term "surrounding".

The term "amphipathic", also referred to as "amphiphilic", refers to a film or membrane having both hydrophobic and hydrophilic groups.

The term "multivalent salt form of at least one alkanoic acid" refers to the salt produced from the reaction of an alkanoic acid and a multivalent cation, at a pH where the alkanoic acid is at least partially, and preferably is mostly, in its dissociated ion form.

The term "multivalent cation" refers to a cation having a charge greater than +1. Examples of inorganic metal cations are those of Group II of the periodic table (e.g., the multivalent cations of Ca, Mg, Fe, and Al).

Preferably, the multivalent cation is Calcium (Ca).

The term "alkanoic acid", refers to an organic carboxylic acid of the general formula R—COOH, wherein R is an aliphatic carbon chain which may be either saturated and/or unsaturated and the —COOH is the carboxylic acid group as known in organic chemistry. The term "alkanoic acid", as defined herein, is used interchangeably with the term fatty acid.

Preferably, the alkanoic acid is a water-immiscible compound. Typically, the R group is an aliphatic chain having a backbone of between 10 and 45 carbon atoms. The backbone may be substituted or unsubstituted. In a preferred embodiment, such optional substitution does not have an effect on the hydrophobicity of the carbon chain.

In a preferred embodiment, the alkanoic acid is an edible alkanoic acid. In one embodiment of the invention, the alkanoic acid is selected amongst alkanoic acids having melting point temperatures higher than 25° C. It should be noted that in outdoor applications, in particular in warm climates, the alkanoic acid is preferably selected amongst alkanoic acids having melting point temperatures higher than 40° C.

Non-limiting examples of saturated alkanoic acids, which may be used in the encapsulation of the solid core comprising the essential oil, and by the method of the invention, are decanoic acid, dodecanoic acid, tetradecanoic acid, hexadecanoic acid, octadecanoic acid, eicosanoic acid, docosanoic acid, and tetracosanoic acid.

Non-limiting examples of unsaturated alkanoic acids which may be used in the encapsulation of the essential oil solid core, by the method of the invention, are 11-octadecenoic acid, 5,8,11,14-eicosatetraenoic acid, omeg-3 fatty acid and others.

Non-limiting examples of omega-3 fatty acids include [alpha]-linolenic acid (18:3-omega-3), octadecatetraenoic acid (18:4-omega-3), eicosapentaenoic acid (20:5-omega-3) (EPA), docosahexaenoic acid (22:6-omega-3) (DHA). docosapentaenoic acid (22:5-omega-3) (DPA), eicosatetraenoic acid (20:4-omega-3), uncosapentaenoic acid (21:5-omega-3), docosapentaenoic acid (22:5-omega-3) including any derivative thereof. In one embodiment, the omega-3 fatty acid is a mixture of two or more such fatty acids. Possible derivatives of omega-3 fatty acids may include ester derivatives, branched or unbranched C1-C30 alkyl esters, branched or unbranched C2-C30 alkenyl esters, or branched or unbranched C3-C30 cycloalkyl esters such as phytosterol esters. In one embodiment, said fatty acids are obtained by extraction from natural sources, including, without being limited to, aquatic organisms such as anchovies, capelin, Atlantic cod, Atlantic herring, Atlantic mackerel, Atlantic menhaden, salmonids, sardines, shark, and tuna; plants such as flax, and vegetables; and microorganisms such as fungi and algae.

Optionally, in addition to the encapsulation of the solid core by the polyurea, polyurethane or amphipathic shell, the micocapsules may be coated by one or more additional layers of a fatty material, such as a wax or a fatty acid.

Thus, according to a preferred embodiment of the present invention, there are provided the microcapsules described hereinabove, further coated by at least one fatty layer, wherein this fatty layer is composed of a fatty material selected from waxes, fats, fatty acids, lipids and low-melting polymers.

In one preferred embodiment, the fatty material is a wax, otherwise known as a fat. The wax can be any hydrocarbon which is solid at room temperature, such as paraffin wax and bee's wax and the like. It may be applied to the surface of the microcapsules either in the melt, or as a solid form, or in other cases from a non-aqueous solution, such as petroleum ether, hexane and the like.

Preferably, the wax is melted, applied to the surface and is then let to solidify to form the required fatty layer.

Examples of waxes obtained from hydrocarbon solvents are paraffin waxes, mineral hydrocarbon waxes, animal waxes (e.g., Beeswax, Chinese, shellac, etc.), Vegetable waxes (e.g., carnauba and Castor wax, Japan waxes, Jojoba oil etc), Mineral waxes (e.g., peat waxes, etc), Petroleum waxes (e.g, paraffin and microcrystalline waxes), synthetic waxes (e.g., Polyethylene waxes—based on polyethylene, Fischer-Tropsch waxes, Chemically modified waxes—usually esterified or saponified, polymerized $\alpha$-olefins etc.

Preferably, the wax is selected from paraffin waxes, mineral hydrocarbon waxes, animal waxes, vegetable waxes, Mineral waxes, Petroleum waxes and synthetic waxes.

Examples of fatty acids, suitable to form a fatty layer according to the present invention, are long chain fatty acids of more than 10 methylene groups and preferably of more than 15 methylene groups, which—when complexed with multivalent ions form film complexes having good release profiles of the encapsulated essential oils, are easily processed in the final product, and are very cost effective. Most preferably, these include, but are not limited to saturated fatty acid molecules, built around a series of carbon atoms linked together in a chain of 12 to 22 carbon atoms chosen from such as stearic acid, heptadecanoic acid tetradecanoic acid hexadecanoic acid, palmitic acid. Preferably, the fatty acid is stearic acid.

Other preferable fatty acids are unsaturated fatty acids such as Myristoleic acid, Palmitoleic acid, Oleic acid, Linoleic acid, $\alpha$-Linolenic acid, Arachidonic acid, Eicosapentaenoic acid, Erucic acid and Docosahexaenoic acid.

Examples of lipids, suitable to form a fatty layer according to the present invention, include, but are not limited to stearic acid, heptadecanoic acid tetradecanoic acid hexadecanoic acid, palmitic acid.

Examples of low-melting polymers, suitable to form a fatty layer according to the present invention, include, but are not limited to polyolefin homopolymers and copolymers of low molecular weight, and polymeric oligomers especially based on ethylene, propylene and alkyl side chain monomers.

The microcapsules of the present invention can be made by several alternative routes.

As shown in Examples 1A, 2A, 3A, 4A, 5A, 6A, 7A, 8A and 9A, the microcapsules are prepared by using combining a solid porous material with one or more essential oils which also contain dissolved therein a monomer or oligomers that are then reacted in an interfacial polymerization reaction.

Thus, according to another aspect of the invention, there is provided a process for the preparation of essential oil solid core microcapsules comprising first dissolving a di- or polyisocyanate into at least one essential oil, as it has been defined hereinabove, to obtain a solution of a di- or polyisocyanate in the essential oil(s).

The essential oil may be encapsulated together with further components selected from adjuvants and agents which enhances the properties of the essential oil, as described in detail hereinabove.

The di- or polyisocyanate is chosen from the group consisting of dicyclohexylmethane 4,4'-diisocyanate; hexamethylene 1,6-diisocyanate; isophorone. diisocyanate; trimethyl-hexamethylene diisocyanate; trimer of hexamethylene 1,6-diisocyanate; trimer of isophorone diisocyanate; 1,4-cyclohexane diisocyanate; 1,4-(dimethylisocyanato) cyclohexane; biuret of hexamethylene diisocyanate; urea of hexamethylene di isocyanate; tri methylene diisocyanate; propylene-1,2-all isocyanate; and butylene-1,2-diisocyanate mixtures of aliphatic diisocyanates and aliphatic triisocyanates are tetramethylene diisocyanate, pentamethylene diisocyanate, hexamethylene diisocyanate and 4-(isocyanatomethyl)-1,8-octyl diisocyanate, aromatic polyisocyanates include 2,4- and 2,6-toluene diisocyanate, naphthalene diisocyanate, diphenylmethane diisocyanate and triphenylmethane-p,p',pt'-trityl triisocyanate. Suitable aromatic isocyanates are toluene diisocyanate, polymethylene polyphenylisocyanate, 2,4,4'-diphenyl ether tri isocyanate, 3,3'-dimethyl-4,4'-diphenyl diisocyanate, 3,3'-dimethoxy-4,4'diphenyl diisocyanate, 1 5-naphthalene, diisocyanate and, 4',4"-triphenylmethane triisocyanate, and isophorone diisocyanate.

This solution is added to a porous solid material, as defined hereinabove, and is mixed until a uniform powder is formed, wherein the essential oil(s) and the di- or polyisocyanate dissolved therein, are both inside the powder.

In order to obtain a uniform encapsulation of the solid core, the mixing is preferably conducted in a rotating drum. Another way would be using fluidized beds but it is a more expensive method.

The essential oil and/or the di- or polyisocyanate are preferably added in one step, by dusting or spraying, or may be separately added to the mixing tank or rotator. Many di- or polyisocyanate have a high volatility and may react with moisture in the air and therefore spraying may not be recommended. However, if no such limitations exist, the di- or polyisocyanate may be added by spraying.

The essential oil and di- or polyisocyanate and any optional additives, may be absorbed within the solid porous core in a water-immiscible liquid. Non-limiting examples of such water-immiscible liquids are alkanes (such as hexane and petroleum ether), ethers (such as diethyl ether, butyl ethyl ether), alcohols, and ketones. AS described above in the preferred method the essential oil acts as the solvent for di- or polyisocyanate and any optional additives.

In a preferred embodiment, the water-immiscible liquid is an edible water immiscible liquid.

To the uniform powder comprising the essential oil(s) and the di- or polyisocyanate, there is added an aqueous solution containing a di- or polyamine and/or a di- or polyhydroxy compound, to effect an interfacial polymerization of the di- or polyisocyanate and the di- or polyamine and/or a di- or polyhydroxy compound.

For example, the interfacial polymerization reaction can be between the di- or polyisocyanate with water and amines, to form a polyurea encapsulating film around the solid core, in a powder form.

The diamine or polyamine is selected from the group consisting of ethylenediamine, diethylenetriamine, propylenediamine Tetraethylenepenteamine, pentamethylene hexamine, alpha, omega-diamines, propylene-1,3-diamine, tetramethylenediamine, pentamethylenediamine and 16-hexamethylenediamine polyethyleneamines, diethylenetriamine, triethylenetriamine, penteethylenehexamine, 1,3-phenylenediamine, 2,4-toluoylenediamine, 4,4'-diaminodiphenylmethane, 1,5-diaminoaphthalene, 1,3,5-triaminobenzene, 2,4,6-triaminotoluene, 1,3,6 triaminonaphthalene, 2,4,4'-triaminodiphenyl ether, 3,4,5-triamino-1,2,4 triazole, bis(hexamethylentriamine) and 1,4,5,8-tetreaminoanthraquinone.

Alternatively, the interfacial polymerization reaction can be between the di- or polyisocyante with di- or polyhydroxy compounds, to form a polyurethane encapsulating film around the solid core, in a powder form.

The di- or polyalcohol is selected from the group consisting of polyhydric alcohols, such as ethylene glycol, dietheylene glycol, propylene glycol, 1,4-butane diol, 1,4 hexane diol, dipropylene glycol, cyclohexyl 1,4 dimethanol, 1,8 octane diol and polyols such as poly(ethylene glycols), poly(propylene glycols), poly(tetramethylene glycols) with average molecular weights in the range of 200-2000, trimethylolpropane, glycerol, hexane, trials and penteerythrytol, 1,3 phenylenedihydroxy, 2,4-toluoylenedihydroxy, 4,4'-dihydroxydiphenylmethane, 1,5-allhydroxyoaphthalene, 1,3, 5-trihydroxybenzene'2,4,6-trihydroxytoluene, 1,3,6-trihydroxynaphthalene, 2,4,4'-trihydroxydiphenyl ether and polyvinyl alcohols.

The interfacial polymerization may be repeated to form additional polyurea and/or polyurethane films encapsulating the solid core.

Thus, according to a preferred embodiment of the present invention, the process described herein further comprises adding an additional amount of a di- or polyisocyanate solution, followed by an additional amount of an aqueous solution containing a di- or polyamine and/or a di- or polyhydroxy compound, as those have been defined hereinabove, to obtain solid core microcapsules doubly coated by a polyurea and/or polyurethane film, in a powder form.

At this stage, the di- or polyisocynate can be dissolved in any non reactive solvent with a boiling point preferable less than 100° C. that is relatively non toxic and inexpensive and with little or no residual water or other reactive contaminates such as amines.

Example of suitable solvents include, but are not limited to, esters, ketones, ethers, and alkyl solvents such as hexane, propane, hetane, pet ethers, etc. Preferably, and as exemplified below, the solvent is ethyl acetate.

The addition of the di- or polyisocyanate solution, and the aqueous solution containing the di- or polyamine and/or a di- or polyhydroxy compound, can be repeated to obtain solid core microcapsules coated by a multiple number of polyurea and/or polyurethane films, in a powder form.

Optimally one polyurea or polyurethane layer is enough to achieve the desired properties of the microcapsules, but if needed, up to 5 such layers may be formed around the solid core, preferably 2-3 coating layers, depending on the application.

The aqueous solution may further comprise a polymerization catalyst.

The catalyst may be selected from the group consisting of amino or organometallic compounds such as N,N dimethylaminoethanol, N—N-dimethylcyclohexylamine, bis-2 dimethylaminoethyl)ether, N—N-dimethylcetylamine, diaminobicyclooctane, stannous octoate and dibutyltin dilaurate having concentration 0.1-0.3 wt. % based on diol and metal salts, tertiary amines such as triethylamine or diethylmethyl amine and metal salts of Cu, Pb, Zn, Co, Ni, Mn.

The aqueous solution may further comprise at least one emulsifier.

Examples of possible emulsifiers include, but are not limited to, Anionic (based on sulfate, sulfonate or carboxylate anions), Perfluorooctanoate (PFOA or PFO) Perfluorooctanesulfonate (PFOS), Sodium dodecyl sulfate (SDS), ammonium lauryl sulfate, and other alkyl sulfate salts Sodium laureth sulfate, also known as sodium lauryl ether sulfate (SLES) Alkyl benzene sulfonate Soaps, or fatty acid salts Cationic (based on quaternary ammonium cations) Cetyl trimethylammonium bromide (CTAB) a.k.a. hexadecyl trimethyl ammonium bromide, and other alkyltrimethylammonium salts Cetylpyridinium chloride (CPC) Polyethoxylated tallow amine (POEA) Benzalkonium chloride (BAC) Benzethonium chloride (BZT) Zwitterionic (amphoteric) Dodecyl betaine Nonionic Alkyl poly(ethylene oxide) Alkylphenol poly(ethylene oxide) Copolymers of poly(ethylene oxide) and poly(propylene oxide) (commercially called Poloxamers or Poloxamines) Alkyl polyglucosides, including: Octyl glucoside Decyl maltoside Polysorbates: Tween 20, Tween 80 Dodecyl dimethylamine oxide.

The process described herein is carried out at a temperature of between 0° C. and 30° C. Preferably the process may be conducted at relatively low temperatures, of less than 15° C., or and in some cases be conducted at room-temperature.

Optionally, around the polyurea or polyurethane film, there may be formed additional layer(s) of fatty materials.

Thus, according to a preferred embodiment of the present invention, the process described hereinabove further comprises mixing the microcapsules containing a solid core, coated by the polyurea and/or polyurethane film(s), with a melted fatty material, as it has been defined hereinabove.

Preferably, the fatty material is a wax, such as paraffin wax or a bee's wax, or stearic acid.

This step may be repeated to obtain solid core microcapsules further coated by a multiple number of fatty layers, to obtain a desired coating thickness, for example 2, 3, 4 and even 5 times.

For example, in Example Test 1 below it can be seen that wax was successfully used at 200% and 400% thickness to modify the coating thickness as desired. In particular, a 100% thickness refers to a single fatty coating while 200% coating refers to the same coating done twice, and 400% coating refers to the same coating done 4 times.

The type of fatty material also determined the properties and release rate of the oil from the microcapsules. The longer chain fatty acids will have better encapsulating properties than the shorter chains and improved stability over temperature. This is related to a reduced water solubility and thus less of a tendency to dissolve in aqueous solutions to which the solid microcapsules may be added (for example in applications to which they must be added to water).

Preferably, in this outer layer of fatty material, there should be a minimal number of unsaturated groups or other highly oxidation-sensitive groups.

As shown in Example 2B, the microcapsules may also be prepared by combining a solid porous material with an alkanoic acid dissolved in essential oil(s) which is then exposed to a mist or spray or solution with a solution of a salt of a multivalent cations, at a pH which is at least above the dissociation constant of the carboxylic groups of the alkanoic acid, thereby forming a form of an encapsulating membrane or film around the solid core by a process of complexation.

Thus, according to another aspect of the invention, there is provided a process for the preparation of essential oil solid core microcapsules comprising first dissolving at least one alkanoic acid with at least one essential oil to obtain a solution.

The alkanoic acid and the essential oil are as described hereinabove.

This solution is then added to a porous solid material, as defined hereinabove, and is being mixed until a uniform powder is formed, which comprises the essential oil(s) and said at least one alkanoic acid. At this stage, the uniform powder may be either dry, wet or partially wet.

As noted hereinbefore for the preparation of the microcapsules via interfacial polymerization, additional additives or adjuvants can be added either with the essential oils, or—with the porous solid material/absorbent, or they can be added after the solid core has been formed.

The essential oil and alkanoic acids, and the optional additives, may also be added to the core of the porous solid material in a water-immiscible liquid. Non-limiting examples of such water-immiscible liquids are alkanes (such as hexane and petroleum ether), ethers (such as diethyl ether, butyl ethyl ether), alcohols, and ketones.

In another embodiment, the solid alkanoic acid is melted before being added to the essential oil or to the water-immiscible carrier.

In a preferred embodiment, the water-immiscible liquid is an edible water immiscible liquid.

Consequently, the uniform powder comprising the essential oil(s) and the at least one alkanoic acid, is mixed with an aqueous basic solution and with an aqueous salt solution comprising at least one multivalent cation.

The aqueous salt solution of this step comprises a mixture of two or more multivalent salts. Such mixtures may be of salts having different cations, e.g., $CaCl_2$ and $MgCl_2$, mixtures of salts having different counter anion, e.g., $CaCl_2$ and $Ca(OH)_2$, or mixtures of salts having cations of different charge, e.g., $CaCl_2$ and $FeCl_3$. In a preferred embodiment, the aqueous salt solution is an edible aqueous salt solution. Non-limiting examples of multivalent organic cations are ammonium salts of di- or tri- or tetra-amines, quarternized polyamines and others. As with the inorganic metal salt solution, the organic salt solution may also comprise two or more different organic salts.

The multivalent cation is as described hereinabove. According to a preferred embodiment of the present invention, the solution of at least one multivalent cation is a mixture of at least two different multivalent cations.

The aqueous basic solution used to react with the alkanoic acids refers to an aqueous solution which is at a pH which is at least above the dissociation constant of the carboxylic groups of the alkanoic acid. This solution may be a solution of a single monovalent base, such as NaOH or a mixture of two or more such bases, e.g., NaOH and KOH, or NaOH and $Na_2CO_3$. In one embodiment, the base is an inorganic base. In another embodiment, the base is an organic base. In a preferred embodiment, the aqueous basic solution is an edible aqueous basic solution.

According to a preferred embodiment of the present invention, the aqueous basic solution is an aqueous solution of at least one of sodium or potassium. Preferably, the aqueous solution of at least one of sodium or potassium is NaOH and/or KOH.

The addition of base and the addition of the multivalent cation can be done either in one step or in two consecutive steps. For example, some multivalent cations, such as Fe, require two separate steps since the multivalent cation will precipitate in basic solutions. On the other hand, when the multivalent cation is Ca, which does not precipitate in a basic solution, one step addition is fine.

Thus, this process also provides microcapsules containing a solid core comprising at least one essential oil mixed with a porous solid material, coated by an amphipathic shell film or membrane, wherein this amphipathic shell is a multivalent salt form of at least one alkanoic acid, in a powder form.

The process described herein is carried out at a temperature of between 0° C. and 30° C. Preferably the process may be conducted at relatively low temperatures, of less than 15° C., or and in some cases be conducted at room-temperature.

Optionally, around the amphipathic shell film or membrane, there may be formed additional layer(s) of fatty materials.

Thus, according to a preferred embodiment of the present invention, the process described hereinabove further comprises mixing the microcapsules containing a solid core, coated by the amphipathic shell film or membrane, with a melted fatty material, as it has been defined hereinabove.

Preferably, the fatty material is a wax, such as paraffin wax or a bee's wax, or stearic acid.

This step may be repeated to obtain solid core microcapsules further coated by a multiple number of fatty layers, to obtain a desired coating thickness, for example 2, 3, 4 and even 5 times, as described hereinabove for microcapsules prepared by the interfacial polymerization.

The microcapsules described herein can be further manipulation after being formed, for example by the addition of a carrier, either solid or liquid.

For example solid carriers, such as additional porous materials, may be added in order to absorb any non-encapsulated essential oil or other active material, or in order to adapt the quantity of the active ingredient to a predetermined quantity (see for example, the addition, of talcum powder in the examples below before placing the microcapsules in sachets for post-harvest applications).

Liquid carriers may be added for better transportation of the microcapsules, or for easier or more convenient application thereof.

For example, the microcapsules of the present invention may be used to treat water bodies either by dusting them in their powder form over the water body, or may be sprayed over the water surface, in which case a liquid carrier has to be added to the microcapsules. Preferably the liquid carrier is water, but other liquid carriers may be used if necessary.

When spraying the microcapsules of the present invention, preferably the microcapsules form a suspension or an emulsion with the liquid carrier, such that following the application of the compositions comprising the microcapsules and the liquid carrier, the solid core microcapsules will act directly with the treatable object, such as a water body, crop etc.

Additional modifications of the microcapsular of the present invention include the addition of any number of additive, adjuvant or additional active ingredient, to the microcapsules.

Therefore, according to another aspect of the invention, there is provided a composition comprising the microcapsules described herein, and optionally further comprising at least one carrier, additive, adjuvant or additional active ingredient.

According to yet another aspect of the invention, there is provided a process for the preparation of this composition, this process comprising preparing the microcapsules of the present invention according to the process described herein and mixing these microcapsules with at least one carrier, additive, adjuvant or additional active ingredient.

It should be noted that for the applications and uses described herein, the microcapsules may be used "as is" or may be used as a composition, further comprising at least one carrier, additive, adjuvant or additional active ingredient.

As detailed in the examples section below, it has now been found that the solid core microcapsules prepared according to the present invention, have a benefit over liquid core microcapsules of the same active components, in that they can stand more vigorous processing conditions and optionally may have different and controllable release profiles which are beneficial in the applications of this invention.

One successful application of the microcapsules of the present invention is in post harvest applications.

As exemplified below, the microcapsules of the present invention have been tested on a variety of crops (for example carrots and peppers) and successfully prevented or limited bacterial and fungal infections as compared to the control of no treatment which had significant bacterial and fungal infections.

Furthermore, the microcapsules of the present invention are advantageous in that they are not in direct contact with the crops. Namely, the solid core microcapsules are put in a cotton-made bag, which is then put in the container with the crop.

Therefore, according to another aspect of the invention, there is provided a method for preventing and/or treating bacterial infections and/or fungal infections in harvested crops by exposing these crops to microcapsules containing a solid core, or to compositions comprising these microcapsules, as those have been defined hereinabove.

Accordingly, according to yet another aspect of the invention, there is provided the use of the solid core microcapsules described herein, as well as compositions containing them, for preventing and/or treating bacterial infections and/or fungal infections in harvested crops.

In particular, it has advantageously been found out that the solid core microcapsules of the present invention, or the compositions comprising them, can be applied while being contained in a closed sachet, thereby preventing any direct contact between the crops and the microcapsules or any of their active ingredients, such as the essential oils. In this case, the crops are being indirectly exposed to the microcapsules or compositions or to the essential oils within the microcapsules or compositions thereof.

The term "sachet" is as generally known in the field of pest control, and is used herein to denote a relatively small bag or envelope-like packet containing the microcapsules of the invention, or compositions comprising them. The sachet is prepared by any woven material, such as cotton, polymer fibers, cellulose derivatives, and synthetic fiber polymers and combinations of such polymers.

For optimal results, the crop should be kept in a closed surroundings, such as a closed room or a closed container, where it will be exposed to the essential oil being released from the microcapsules contained in the sachet.

Of course, it is clear to any person skilled in the art that the microcapsules may be applied in a conventional manner, such as spraying, dipping or dusting or any combination of different methods, either in parallel or in sequence.

The amount of material in a sachet is determined according to the type of essential oil(s) and additional active ingredients, the percentage of active ingredient within each microcapsule, the type of crop to be treated and the size and type of the surroundings where the crop is located. However, generally, the amount should be calculated such that the each sachet will contain at least 1% of active ingredient in relation to the weight of the crop, when the crop is in a closed surroundings. Preferably, the sachet should contain at least 5% of active ingredient in relation to the weight of the crop.

This amount can be contained in one sachet or may be divided between several sachets, such that the amounts given above will be the overall amounts of all sachets combined.

The crops suitable to be treated by the microcapsules of the invention are selected from, cereals, beans and peas, fruits, vegetables, root crops, processing crops, cucurbitaceous plants, pasture plants, lawn grasses; perfumery crops; flowers and ornamental plants, garden-trees and timber woods. In each of these cases, the treatment can be to the leaves, bark, fruit, flowers, seeds, or roots of the crops.

Examples of cereals include, but are not limited to, rice, barley, wheat, rye, oat, corn, etc.

Examples of beans and peas include, but are not limited to, soybean, red bean, broad bean, pea, kidney-bean, peanut, etc.

Examples of fruits include, but are not limited to, apple, citrus, pear, grape, peach, plum, cherry, walnut, chestnut, almond, banana, strawberry, etc.

Examples of vegetables include, but are not limited to, cabbage, tomato, spinach, broccoli, lettuce, onion, stoneleek, Spanish paprika, eggplant, pepper, etc.

Examples of root crops include, but are not limited to, carrot, potato, sweet potato, taro, radish, lotus rhizome, turnip, burdock, garlic, etc.

Examples of processing crops include, but are not limited to, cotton, flax, beet, hop, sugarcane, sugar beet, olive, gum, coffee, tobacco, tea, etc.

Examples of cucurbitaceous plants include, but are not limited to, pumpkin, cucumber, muskmelon, watermelon, melon, etc.

Examples of pasture plants include, but are not limited to, orchard grass, sorghum, timothy, clover, alfalfa, etc.

Examples of garden-trees include, but are not limited to, ginkgo tree, cherry tree, gold-leaf plant, etc.

Examples of timber woods include, but are not limited to, white fir, silver fir, pine, hatchet-leaved arbor-vitae, Japan cedar, Japanese cypress, etc.

The bacterial infections treated by the microcapsules of the present invention include infections caused by bacteria selected from e-coli, pseudomonas arginosa, streptococus, stefalococus aurus and arachinom bateria. Optionally, the microcapsules of the present invention are effective against infections caused by *Erwinia* bacteria (belonging to the Enterobacteriaceae genus).

It has been found that the microcapsules of the present invention have been effective against several types of fungi, such as *Rhizopus* and *Butritis*. It is further expected that these microcapsules will be effective fungicides against additional fungi species, such as for example *Alternaria* and *Kaladosporium*.

Preferably, the microcapsules contain essential oils having antibacterial and/or antifungal properties. Examples of such essential oils include, but are not limited to, oregano oil, tea tree oil, eucalyptus oil, thyme oil, rosemarine oil and any combination thereof.

The microcapsules or compositions comprising them may further contain at least one other natural or synthetic fungicide, nematicide, IGR or bactericide to enhance the activity of the essential oil.

According to a preferred embodiment of the present invention, all of the components used to prepare the microcapsules used for the treatment and/or prevention of bacterial and/or fungal infections of crops, are made from natural sources. In this case, the method can be considered a "green" or natural method for the treatment and/or prevention of bacterial and/or fungal infections of crops.

Similarly, the microcapsules of the present invention, as well as compositions comprising them can also be used to treat other additional products that are likely to grow fungi or bacteria, such as food products, leather products, fur coats and products of paints and pastes formed of starch or cellulose, thereby increasing the shelf life of these products. Such microcapsules possess similar benefits as those of the microcapsules used in post harvest treatment, namely:

a) the use of natural rather than synthetic active ingredients;

b) the ability to treat the products without direct contact therewith; and c) the controllable release rate of the active essential oils and additional active ingredients, which enables using lower amounts thereof, and is therefore very cost effective.

As can be seen in Examples Test 2 and Test 3 below, the microcapsules of the present invention were further incorporated in various plastic materials for a variety of applications.

For example, the microcapsules were incorporated into veterinary products, such as animal collars, where they successfully deterred flies, fleas and ticks from a variety of farm and household animals, such as dogs, horses and cows. In another example, they were incorporated into a plastic tablecloth and successfully deterred flies around the treated area.

In these examples and in similar cases, the microcapsules of the invention or compositions comprising them were melted and extruded into various molds, together with the plastic materials used for preparing these plastic table cloths, or these plastic collars, for example polyethylene.

The same method can be extended to a large number of plastic products for purposes of deterring pests and/or preventing infestation by these pests and/or treating animals infected by these pests.

The term "plastic products" refers to any organic polymer that is moldable and extrudable and can assume an infinite variety of forms and shapes according to its specific use or application.

Preferable plastic products for the purpose of the present invention are household plastic products, outdoor plastic products and veterinary plastic products.

The polymers suitable to be used for preparing any of these plastic products are any extrudable polymer compositions. Any polymer or polymer blend that may be extruded, with or without application of pressure, is suitable in the purpose of the present invention. Thermoplastic polymers (polymers that soften when exposed to heat and return to their original condition when cooled to room temperature) are particularly suitable, examples of which are polyvinyl chloride, polyethylene, polypropylene, polyvinyl acetate, polyester polymers, for example, poly(ethylene terephthalate), ABS copolymers, polyamides, for example nylon.

A preferred class of extrudable polymers is represented by elastomeric (rubbery) polymers, in particular thermoplastic elastomers which do not require vulcanization but are shaped above their softening temperature and develop elastomeric properties upon cooling. Examples of satisfactory thermoplastic elastomers are polyurethane-polyester elastomers, segmented polyethers and polyesters, nylon block polymers, styrenic block thermoplastic elastomers and dynamically cured blends of polyolefin resin and monoolefinic rubber.

Vulcanizable elastomers comprise another class of extrudable polymers, especially vulcanizable diene-containing elastomers. Either natural or synthetic rubbers or mixtures thereof are satisfactory. However, non-diene rubbers, like silicone rubbers or fluorinated rubbers are also satisfactory. Illustrative examples of suitable synthetic rubbers include cis-4-polybutadiene, butyl rubber, neoprene, ethylene propylene terpolymers, polymers of 1,3-butadiene, polymers of isoprene, ethylene vinyl-acetate copolymers and copolymers of 1,3-butadiene with others monomers, for example, styrene, acrylonitrile, isobutylene and methylmethacrylate.

Preferably, the plastic products impregnated with the solid core microcapsules of the present invention are prepared by extruding and/or molding the solid core microcapsules, or the compositions comprising them, together with the plastic material used for preparing similar non-impregnated products.

The conditions of such extrusions and/or moldings are known to a person skilled in the art. Preferably, the microcapsules are mixed as a powder with the relevant polymer and the mixture is then extruded.

Alternatively, the microcapsules are first melted and are then mixed or blended together with the molten polymer used for the process.

The weight ratio of the microcapsules or composition comprising them, as part of the polymer from which the plastic product is being prepared, is determined on a case-by-case basis, depending on the specific application, type of polymer etc.

Generally, however, the microcapsules are incorporated in the plastic products in a ratio ranging from 2 to 50% w/w relative to the polymer. More preferably, this ratio ranges from 5 to 30% w/w.

As noted hereinabove one specific application for the plastic products impregnated with the microcapsules of the present invention or compositions comprising same, is a veterinary use.

Thus, according to one aspect of the invention, there is provided a method for preventing and/or treating pesticidal infestation in animals by incorporating the solid core microcapsules, or compositions comprising them, as those have been described herein, in plastic veterinary products.

The term "preventing and/or treating pesticidal infestation" further includes deterring certain animal pests, wherein the term "pest" as used herein includes, but is not limited to, flees, ticks, ants, cockroaches, flies, mosquitoes, moths etc.

The term "preventing and/or treating pesticidal infestation" further includes disinfection of surfaces with which the animals come into contact, such as mats, rugs, and bedding materials for animals.

The term "veterinary products" as it is used herein includes, but is not limited to, animal collars, mats, rugs, cloths and bedding materials for animals.

The animals that can be treated by this method can basically be any domesticated animal, farm animal or zoo animal, which is prone to a pesticidal infestation.

For examples, this method can be applied to animals such as, but not limited to, dogs, cats, rabbits, hamsters, horses, cows, livestock, fowl (i.e., chickens, turkeys, pheasants etc.) and zoo animals.

The collars, or other veterinary products, impregnated with the microcapsules of the present invention, exhibit the following benefits:
a) The active ingredients are released at a controllable release rate, which can be pre-determined according to the specific need;
b) The controllable release rate of the active ingredients allows using lower amounts of the active ingredient, and thus-create a more cost effective product;
c) Supplying an impregnated veterinary product is a relatively simple procedure as compared to actively disinfecting an animal;
d) The frequency of treatment of the animal is minimized since the impregnated veterinary product, which slowly and controllably releases the active ingredients, is replaced once over a period of weeks and months, rather then conducting several such treatments in conventional methods; and;
e) The impregnated veterinary products can be completely "green", thereby circumventing the need to use undesirable synthetic disinfectants.

Thus, according to another aspect of the invention, there are provided plastic veterinary products impregnated with solid core microcapsules, or compositions comprising them, as those have been described hereinabove.

There is also provided the use of the solid core microcapsules described herein, or compositions comprising them, for preventing and/or treating pesticidal infestation in animals.

As further noted hereinabove other specific applications for the plastic products impregnated with the microcapsules of the present invention or compositions comprising same, are household and outdoor applications.

Household applications may include deterring, preventing and treating pest infestations within the house, office, public institution etc., and in their surroundings. Plastic products for such uses include mattresses, curtains, plastic fibers of clothing, tablecloths, plastic bins, garbage bags etc.

Outdoor applications may include deterring, preventing and treating pest infestations in open spaces, such as around picnic areas, camping sites, around schools or other public institutions, outdoor events location etc. Suitable plastic products for outdoor use include, but are not limited to, tents, picnic tablecloths, garbage bins etc.

Thus, according to another aspect of the invention, there is provided a method for repelling pests in an environment, this method comprising incorporating the solid core microcapsules of the present invention, or compositions comprising them, as those have been described herein, in plastic household products or plastic outdoor products.

The term "pest", as used herein refers to any organism capable of transmitting the causative agent of human or animal disease or capable of producing human or animal discomfort or injury, including insects, rodents etc. Specific examples include, but are not limited to, mosquitoes, flies, fleas, cockroaches, ants, mites, moths, worms, ticks or other insects or rats.

This method may be used to prevent or deter the following pests from the area in which the microcapsules are being used: mosquitoes, flies, fleas, cockroaches, ants, mites, moths, worms, ticks or rats etc.

The term "environment" as used herein refers to a predefined physical area which is requested to be free of pests. The environment can be both indoors and outdoors.

The size of the environment treatable by the microcapsules of the present invention is determined by the type and concentration of the active ingredient, and on the required tolerance of pests within this area.

According to yet another aspect of the invention, there are provided plastic household products and plastic outdoor products impregnated with solid core microcapsules or compositions comprising them, as those have been described hereinabove.

Alternatively, the microcapsules of the present invention, as well as compositions comprising them may be applied in their solid form, similarly to the post-harvest applications, to achieve the same purpose of deterring pests, whereas the active essential oils and/or additional ingredients are placed in closed sachets in or around the area(s) to be treated.

Thus, according to another aspect of the invention there is provided a method for repelling pests in an environment, this method comprising placing a closed sachet comprising the solid core microcapsules of the present invention, or compositions comprising them, as those have been described herein, in this environment.

Thus, there is also provided the use of the solid core microcapsules described herein, or compositions comprising them, for repelling pests in an environment.

Finally, another important application of the microcapsules of the present invention is the treatment of water bodies, in particular water bodies used for drinking water or water for other domestic use.

Water bodies may be infested with larvae or eggs of a variety of insects or may contain other forms of life, such as zooplankton, which are undesirable in drinking water and in water for other domestic use.

Known methods to treat water bodies often use synthetic pesticides, but finding residues of these chemicals in drinking water is obviously unwanted.

Alternatively, using natural pesticides requires very large quantities of which to be effective, and also is not effective for targeting species which reside at the bottom of the water bodies or at varying depths in it.

As can be seen in Example Test 4, the microcapsules of the present invention were successfully used to prevent the growth of chironomide (*Chironomus*) larvae and crustaceans, such as copepods, in various water bodies.

This was achieved by designing the density of the microcapsules of the present invention, or compositions comprising them, to be greater than 1, the density of water, so that these microcapsules or compositions comprising same, will sink to the bottom of water bodies, or will sink to another predetermined depth, according to the site of the water pest to be treated.

The ability to control the density of these microcapsules or compositions comprising same depends on:
a) the identity (and hence the density) of the porous solid material composing the solid core of the microcapsules;
b) the weight ratio between this porous solid material and the essential oils; and
c) the release rate of the essential oil from the solid core f the microcapsules.

Thus, according to one aspect of the invention, there is provided a method for treating water bodies, said method comprising adding the solid core microcapsules of the present invention, or compositions comprising them, as those have defined hereinabove, to a water body containing at least one water pest.

The term "water body" includes, but is not limited to, drinking water bodies and reserves, lakes, ponds, reservoirs, streams, rivers, and recreational areas such as swimming pools.

The term "water pests" refers to zooplankton, aquatic insects and algae.

Zooplankton is a term describing microscopic animals that eat other plankton. It is a broad categorization spanning a range of organism sizes, from small protozoans to large metazoans. It includes holoplanktonic organisms whose complete life cycle lies within the plankton, and meroplanktonic organisms that spend part of their life cycle in the plankton before graduating to either the nekton or a sessile, benthic existence.

Examples of zooplankton treatable by the present method, include but are not limited to, small crustaceans, such as copepods and foraminiferans, radiolarians and dinoflagellates, chaetognaths (arrow worms), molluscs and chordates, such as salps and juvenile fish.

The term "aquatic insects" refers to insects selected from, but not limited to, mosquitoes, *Chironomus, Collembola, Ephemeroptera, Odonata, Plecoptera, Hemiptera, Neuroptera/Megaloptera, Trichoptera, Lepidoptera* and *Coleoptera*. In particular, this term includes the larvae and eggs of these insects.

Examples for suitable algae treatable by the microcapsules of the present invention, include, but are not limited to, red algae.

An advantage of the present method is that both the location of release, and the time-release profile can be adjusted for maximizing the efficacy and cost effectiveness of the essential oil compositions, as pesticides in water applications.

The active ingredients in microcapsules suitable for water treatment applications are essential oils, such as but not limited to, citronella oil, pine oil, clove oil, tea tree oil, eucalyptus oil and oregano oil, insect growth regulators (IGRs), such as Azadirachtin, Pyriproxyfen etc., and any combinations thereof, that have good efficacy to reduce the Chironomides and zooplankton to acceptable heath and esthetic levels.

These active ingredients are used at concentrations ranging from 0.1 to 30% by weight of the microcapsular composition.

It should be noted that according to a preferred embodiment of the present invention, the microcapsules contain green IGRs, which are IGRs of natural sources, such as for example Neem oils, and individual fractions extracted from these natural IGRs, such as azadirachtin derived from Neem oils.

According to the method presented herein, the microcapsules of the present invention, as well as compositions comprising them, were applied at a concentration of about 10 ppm in the water bodies.

Important characteristics and advantages of the obtained microcapsules or compositions comprising same, include:
a) The microcapsules can have a density which is greater than 1 and therefore be pre-designed to sink to the bottom of water body, or descend to varying depths below the surface, according to the site of the targeted water pest or zooplankton. However, if desired, the microcapsule can just as well be pre-designed to float on the surface of the water, or sink just below it, for example when the density of the microcapsules is about 1, and only slightly above it. This can be achieved by choosing the type and quantity of the porous solid material, absorbing the active ingredients within the solid core of the microcapsules;
b) The active ingredients are a combination of essential oils and insect growth regulators that have good efficacy to reduce the Chironomides and zooplankton to acceptable heath and esthetic levels;

For the various application described herein the sold product may be provided in a kit or a commercial package comprising the microcapsules of present invention, and optionally comprising a carrier.

The kit comprising the microcapsules or the composition of the present invention may be presented in a solid or a liquid form, either in a concentrated or a diluted state and may be applied to the target environment or product by, for example, a sponge or a piece of cloth, which was pre absorbed by the composition, or by hand-held spray.

Optionally, the kits of the present invention may also comprise instructions how to apply the components thereof to the target environments or products, as to achieve the desirable effect for a given applications. The kits may also contain different components and instructions for different applications.

EXAMPLES

Reference is now made to the following examples, which together with the above descriptions, illustrate the invention in a non limiting fashion.

In particular, it should be emphaisized that the concentrations of essential oils and additional components are not to be regarded as limiting concentrations, and serve merely for the purpose of presenting the examples, and additional concetrations may be used.

For simplicity, throughout the examples, the term "formulation" is widely used and encompasses the microcapsules of the present inventions, as well as compositions containing these microcapsules and optionally containing additional ingredients. A person skilled in the art would be able to understand from each example, to what does the term "formulation" refer to in each case.

Materials and Analytical Methods

Tea tree oil, Oregano oil, Pine oil, Citronella oil, Pyrethrum and Cotton seed oil were obtained from Tamar Marketing Company.

Toluene 2,4 diisocyanate (T.D.I), Ethylene diamine (EDA) and Diethylene triamine (DETA) were obtained from Fluka in a technical grade.

Polymethylene Polyphenylisocyanate (Voronate 220) was obtained from Dow Chemicals.

Aerosil A 200 and Aerosil A 300 were obtained from Degussa A. G Frankfurt Del.

Qwenling (essential oil from lemon eucalyptus) was obtained from Shiffon Ltd.

Dimilin was from Shifon Ltd Luxemberg.

Azadirachtin was obtained from OzonoBiotec division of Shivanshu Sintered Products of India.

*Chironomus* larvae and eggs and Copepods were obtained from the Faculty of Agriculture in Rehovot.

All other chemicals were purchased from Sigma-Aldrich and were used without further purifications.

The preparation of the microcapsules was done using rotating multiplex production drum (6005/mum Multiplex-Apex Construction LTD London).

Weighting was conducted using a semi analytical balance by Defibnes.

HPLC measurements were conducted on a Shimadzu HPLC with adjustable UV detector (Column for example: Luna 5μ phenyl-Hexyl: 250×4.6 mm 5μ).

All percentages below are weight percentages.

Example 1A: Preparation of Solid Core Microcapsules Containing 64% Tea Tree Oil, by Interfacial Polymerization A solid core formulation containing 64% tea tree was prepared as follows:

First, toluene diisocyanate (TDI, 22.8 grams, 0.12 moles) was dissolved in tea tree oil (181.2 grams) to produce a 24 M TDI/tea tree oil solution.

Separately, ethane diamine (EDA, 5.4 grams, 0.18 moles) was mixed with diethylene triamine (DETA, 4.7 grams, 0.046 moles) in water (10.6 grams) to produce a 21.3 M EDA/DETA aqueous solution.

AEROSIL 300 (70 grams) was then placed in a rotating multiplex production drum and the TDI/tea tree oil solution was added thereto in one step and the drum was rotated for 60 minutes to obtain a uniform absorption into the Aerosil A 300 powder. The aqueous EDA/DETA solution was then sprayed into the drum and was rotated for additional 2 hours to obtain an encapsulated tea tree oil solid core formulation, in a powder form.

The same reaction was repeated, substituting the TDI with Polymethylene Polyphenylisocyanate (Voronate 220).

In addition the following formulations were also prepared according to this example.
A) Microcapsules containing Citronella oil (20-25% w/w of the total formulation weight) and Pyrethrum (2-4% w/w of the total formulation weight) for veterinary applications and environmental applications below.
B) Qwenling (20-25% w/w of the total formulation weight) and Pyrethrum (2-4% w/w of the total formulation weight) for environmental applications below.
C) Formulations W1-W4 (containing pine oil, Pyrethrum, oregano oil, Dimilin, Azadirachtin) used for water applications below:
Formulation #W1, where instead of tea tree oil contained Pine oil (180 grams) with Pyrethrum (18 grams) and Dimilin (18 grams);
Formulation #W2, prepared according to Example 1A where instead of tea tree oil containing Oregano oil (90 grams), Pine oil (90 grams, 18.3%), Pyrethrum (18 grams) and Dimilin (18 grams); Formulation #W3, prepared according to Example 1A were instead of tea tree oil contained Pine oil (180 grams), Pyrethrum (18 grams) and Azadirachtin (14 grams);
Formulation #W4, containing Pine oil (105 grams), Oregano oil (75 grams), Pyrethrum (18 grams) and Azadirachtin (14 grams).

Example 1B: Preparation of Solid Core Microcapsules Containing 64% Tea Tree Oil, by the "Green" Method The microcapsule powder was also formulated in an aqueous carrier, as follows:

Decanoic acid (12 grams, 0.07 MOLES) was dissolved in tea tree oil (100 grams) and this solution was added to a rotating drum containing Aerosil A 200 (70 grams) and rotated for 60 minutes at a speed that gives a uniform distribution. After this time, a solution containing NaOH (3.5 grams, 0.09 MOLES) and $CaCl_2$ (7 grams, 0.063 MOLES) in water (100 ml) was sprayed into the rotating drum and rotated for an additional two hours to produce a solid core microcapsular powder containing 64% tea tree oil.

Example 2A: Preparation of Solid Core Microcapsules Containing 64% Oregano Oil, by Interfacial Polymerization Example 1A was repeated using Oregano oil (134 grams) instead of tea tree oil to give a solid particle formulation containing 64% oregano.

Example 3A: Preparation of Solid Core Microcapsules Containing 32% Oregano Oil and 32% Tea Tree Oil, by Interfacial Polymerization Example 1A was repeated using a mixture of tea tree oil (67 grams) and oregano oil (67 grams) resulting in a weight ratio of 1:1 of the essential oils instead of only tea tree oil as in example 1, to give a solid particle formulation containing 32% tea tree oil and 32% oregano oil of the same weight as in example 1.

Example 4A: Preparation of Solid Core Microcapsules Containing 64% Oregano Oil by Interfacial Polymerization, Further Coated by Paraffin Wax Microcapsules containing two stages of coating (polymeric coating, and final wax coating) were prepared as follows:

Example 2A was repeated using the following quantities: 51 grams of Aerosil A 300, 67 grams of TDI, 134 grams of oregano oil, a mixture of 30 grams EDA and 14 grams DETA, in 30 ethyl acetate (EA).

After obtaining the solid core microcapsular powder containing 64% oregano oil, with the interfacial coating made with TDI, melted paraffin wax (10 grams) was added into the rotator, to coat the aforementioned particles and was kept under mixing for an additional hour to ensure the complete evaporation of the ethyl acetate. A doubly coated powder was obtained, having an increased coating thickness and a decreased volatility of the powder, which can be tailor-made to achieve a desired controlled-release rate.

A sample as above was made with slight variations in the components and labeled 1-ETW with the component concentrations used in the preparation given in the Table below. It should be noted that EA (ethyl acetate) is removed by evaporation.

| Order of operations | Material | Weight (grams) |
|---|---|---|
| 1 | Aerosil 300 | 51.83 |
| 2 | Oregano oil | 134 |
|  | TDI | 67.6 |
| 3 | DETA | 12 |
|  | EDA | 14 |
|  | EA | 30 |
| 4 | Paraffin wax | 10 |
|  | Total | 289.43 |
|  | (without the weight of the volatile EA) |  |
|  | Total real due to mass loss from transferring from one flask to another | 238 |

Example 5A: Preparation of Solid Core Microcapsules Containing 64% Mixtures of Oregano Oil and Tea Tree Oil, by Interfacial Polymerization, and Coated by Paraffin Wax Example 4A was repeated using different ratios of oregano oil and tea tree oil to obtain solid core microcapsular powders containing 64% of the following oregano oil and tea tree oil weight ratios: 50/50, 20/80 and 80/20, as appears in the table below:

|  | Active Ingredient (%) | |
|---|---|---|
| Sample | Oregano oil | Tea tree oil |
| 1-ETW | 100 | — |
| 2-ETW | 50 | 50 |
| 3-ETW | 20 | 80 |
| 4-ETW | 80 | 20 |

Example 6A: Preparation of Solid Core Microcapsules Containing 64% Mixtures of Oregano Oil and Tea Tree Oil, by Double Interfacial Polymerization, and Further Coated by Paraffin Wax (Double Thickness)

Example 5A was repeated (quantities: 51 grams Aerosil A 300, 22.4 grams TDI, 134 grams oregano oil) with the difference that after the EDA (4.6 grams)/DETA (4 grams) acetate solution (20 grams) was sprayed and rotated, the interfacial polymerization step was repeated by spraying a second layer of TDI (11.4 grams) in ethyl acetate (5%) on the rotating particles, followed by an additional spraying of EDA (2.4 grams)/DETA (2 grams) ethyl acetate solution (10 grams), to obtain doubly coated solid core microcapsules. The final coating of paraffin wax (20 grams) was also applied as in example 5A, but doubling the amount of the wax, thereby increasing the thickness of the powder accordingly. This example was repeated using different ratios of oregano oil and tea tree oil to obtain solid core microcapsular powders containing the following ratios:

|  | Active Ingredient (%) | |
|---|---|---|
| Sample | Oregano oil | Tea tree oil |
| 5-ETW | 100 | — |
| 6-ETW | 50 | 50 |
| 7-ETW | 80 | 20 |
| 8-ETW | 20 | 80 |

For example, the composition of formulation 8-ETW is given below:

| Order of operations | Material | Weight (grams) |
|---|---|---|
| 1 | Aerosil 300 | 51.83 |
| 2 | Oregano oil | 26.8 |
|  | Tea Tree oil | 107.2 |
|  | TDI | 22.4 |
| 3 | DETA | 4 |
|  | EDA | 4.6 |
|  | EA | 20 |
| 4 | TDI | 11.4 |
| 5 | DETA | 2 |
|  | EDA | 2.4 |
|  | EA | 10 |
| 6 | Paraffin wax | 20 |
|  | Total | 256.63 |
|  | Total real | 248 |

Example 7A: Preparation of Solid Core Microcapsules Containing 64% Mixtures of Oregano Oil and Tea Tree Oil, by Double Interfacial Polymerization, and Coated by Bee Wax Example 6A was repeated, whereas the paraffin wax was replaced with bee's wax, which was melted prior to application.

Example 8A: Preparation of Solid Core Microcapsules Containing 64% Mixtures of Oregano Oil and Tea Tree Oil, by Double Interfacial Polymerization, and Coated by Stearic Acid Example 6A was repeated, whereas the paraffin wax was replaced with stearic acid, which was applied in the melt form or as a 10% W/W solution in ethyl acetate.

The formulations prepared according to Examples 7A and 8A, containing oregano oil only, are presented in the table below:

The formulations are made first by the double interfacial polymerization (as described in example 6A) and then coated by either wax (9-ETBW and 10-ETBW Table below) or with stearic acid (11 and 12-ETBW Table below) instead of the wax.

| Sample | Coating material | Coating thickness (%) |
|---|---|---|
| 9-ETBW | Bees wax | 100 |
| 10-ETBW | Bees wax | 200 |
| 11-ETSt | Stearic acid | 100 |
| 12-ETSt | Stearic acid | 200 |

Example 9A: Preparation of Solid Core Microcapsules Containing 64% Mixtures of Oregano Oil and Cotton Seed Oil, by Double Interfacial Polymerization, and Coated by Stearic Acid Example 8A was repeated, whereas cotton-seed oil was added to the oregano oil in order to significantly reduce the evaporation rate of the latter from the encapsulated microcapsules. The quantities used were: a mixture of oregano (107.2 grams) with cotton-seed oil (26.8 grams), 44.8 grams of TDI, 51.8 grams of Aerosil 300, 20 grams of ethyl acetate solution of EDA (9.2 grams)/DETA (8 grams), and for a second IP coating a 5% solution of TDI (22.8 grams) in ethyl acetate, a spray of DETA (4.8 grams)/EDA (4 grams) in 10 grams ethyl acetate (EA). The obtained microcapsules were sprayed by melted stearic acid (20 to 40 grams).

The various prepared formulations are described in the table below, reflecting changes in the amount of stearic acid (and thereby determining the thickness of the coating), as well as changes in the amount of cotton seed oil. Samples 13-ETSt and 14-ETSt are samples prepared by one stage of interfacial polymerization, whereas samples 15-ETSt and 16-ETSt were prepared by double interfacial polymerization.

| Sample | Coating thickness (%) | Additional remarks |
|---|---|---|
| 13-ETSt | 400 | Including 10% cotton seed oil |
| 14-ETSt | 400 | Including 20% cotton seed oil |
| 15-ETSt | 200 | Including 10% cotton seed oil double interfacial polymerization |
| 16-ETW | 200 | Including 10% cotton seed oil double interfacial polymerization |

For example, the composition of formulation 16-ETW is described in the table below:

| Order of operations | Material | Weight (grams) |
|---|---|---|
| 1 | Aerosil 300 | 51.83 |
| 2 | Oregano oil | 107.2 |
|  | Cotton oil | 26.8 |
|  | TDI | 44.8 |
| 3 | DETA | 8 |
|  | EDA | 9.2 |
|  | EA | 20 |
| 4 | TDI | 22.8 |
| 5 | DETA | 4 |
|  | EDA | 4.8 |
|  | EA | 10 |
| 6 | Paraffin wax | 20 |
|  | Total | 299.43 |
|  | Total real | 286.7 |

Oil release tests were conducted using the same kind of bags used for the efficacy tests, and the tests were carried out in refrigerated storage at 6° C. and 80% humidity. The microcapsules containing oregano oil and cotton seed oil mixtures had a significantly reduced (by about 80%) rate of oregano oil release, as compared to microcapsules containing oregano oil only.

It has been observed that when the cotton seed oil (plant oil) was added to the essential oil and then encapsulated together the release rate of the oregano was significant longer than for a control microcapsule with only oregano oil.

Example Test 1: Post Harvest Application of Solid Core Microcapsules

General Methods:
Post Harvest Efficacy Tests

In order to evaluate the efficacy of the microcapsules in preventing *Rhizopus* and/or *Botrytis* fungal infections in harvested crop, biological activity experiments were conducted on red peppers.

The peppers were collected 3 days prior to testing and have not been pre-treated whatsoever.

The fruits were placed in commercial polyethylene bags, called Hachotrim bags and prepared to contain the post harvest peppers. Each bag contained 6 peppers and two cotton-made formulation bags (5 cm×5 cm), each containing 5 grams of formulation. The formulations had been mixed with talc powder in order to decrease the quantity of the active ingredient to 6%, the minimal effective concentration of fungicide.

Each experiment was composed of 5 repetitions of every formulation sample, as well as 5 repetitions of control samples (containing no fungicide).

Three sets of experiments were done.

Visual testing of the samples was conducted once a week for 35 days, to determine the development of rotting, and the results were recorded with readily available quality control software.

During the experiments, the peppers were kept at 6° C., 60-70% humidity and under atmospheric pressure in a laboratory industrial refrigerator.

Some formulations were further tested by conducting another experiment on fresh samples, over 42 days, with 10 repetitions of every formulation sample, as well as 5 repetitions of control samples (containing no fungicide). The rest of the parameters are as described hereinabove.

Taste Tests

In order to confirm that microcapsules containing fungicides do not damage the taste of the treated fruits or vegetables, a taste test experiment was conducted by collecting 30 peppers undamaged treated and non-treated specimens, 35 days after beginning of the treatment, storing them in a refrigerator for 24 hours, and then washing and cutting them onto plates marked by serial numbers. The specimens were tasted by 15 individuals, who were asked to indicate any sign of aftertaste.

Oil Controlled-Release Experiments

Controlled release experiments were carried out by determining the amount of essential oil remaining in each formulation using HPLC.

16 formulations were tested over 6 weeks (overall 96 experiment bags). Each bag contained 5 cotton bags (5 repetitions) containing 5 grams of the same formulation (6% diluted by talcum powder). Each week 16 samples one of each formulation, were taken for analysis, such that all repetitions were combined for the analysis.

During the experiments, the peppers were kept at 6° C., 60-70% humidity and under atmospheric pressure in a laboratory industrial refrigerator.

Post Harvest Results

A. Efficacy Tests
A) The obtained powder prepared according to Example 1A (by interfacial polymerization), containing 64% tea tree oil, was applied as described above in Post Harvest efficacy test on carrots within a post harvest container. Visual observation after 3 weeks showed that the treated powder formulation had prevented bacterial and fungal infections as compared to the control of no treatment which had significant bacterial and fungal infections.
B) The obtained powder prepared according to Example 1B (by the green method), also containing 64% tea tree oil, are applied to the carrots as in "A" above. The funguses *Rhizopus* and *Butritis* were checked visually by an expert agronomist with many years of experience.
C) The obtained powder prepared according to Example 2A (by interfacial polymerization), containing 64% oregano oil, was applied as described above in Post Harvest efficacy test on potatoes within a post harvest container. Visual observation after 3 weeks showed that the treated powder formulation had prevented bacterial and fungal infections as compared to the control. This is a paper example and visual observation.
D) The obtained powder prepared according to Example 3A (by interfacial polymerization), containing 32% tea tree oil and 32% oregano oil was applied as described above in Post Harvest efficacy test on potatoes within a post harvest container, and over a two week period visual observation showed that it prevented bacterial and fungal infections as compared to the control.
E) The obtained powder prepared according to Example 4A (by interfacial polymerization), containing 64% oregano oil, and coated by paraffin wax acid, was tested in efficacy tests over a period of 35 days on 30 peppers divided into 5 bags where each bag contains 2 small bags with 5 grams of the formulation. In each of the small bags with the 5 g microencapsulated essential oil was diluted with talcum powder to dilute the amount of essential oils in the total formulation to 6% essential oil Each week the peppers were visually observed to determine *Rhizopus* and *Botrytis* infection. The encapsulated essential packages reduced the number of peppers with bacterial growth by more than 50% to 80% and in some cases 90%.

Furthermore, taste tests by 15 different tasters chosen randomly, of the treated peppers more than 80% claimed that the taste of the peppers was as if they were picked fresh.
(F) Microcapsules prepared according to Example 5A were tested on peppers as described in Example 1E above.

The development of fungi (*Rhizopus* and *Botrytis*) growth on the stem of the peppers treated by formulations 2-ETW and 3-ETW, prepared in Example 6A, over a period of 35 days was studied. It was observed that no fungi have grown on any sample including the control for the first 21 days. After 21 days the control and 3-ETW there is a slow increase until the $28^{th}$ day, and a sharper increase thereafter wherein at 35 days the control has a 53% infection while 3-ETW exposed samples a 20% infection. The peppers treated with 2-ETW had less than 5% infection at days, thus indicating that a higher ratio of oregano/tea tree gives better results.

(G) The microcapsules prepared according to Example 6A were tested on peppers as described in Example 1E against *Rhizopus* and *Botrytis*. The results obtained by visual observation showed good inhibition against *Rhizopus* and *Botrytis* growth similar to the results in example (F).

Furthermore, all 15 taste testers of the treated peppers revealed that the taste of the peppers was as if they were picked fresh.

(H) The microcapsules prepared according to Example 7A were tested on peppers as described in Example 1E against *Rhizopus* and *Botrytis*. The results obtained by visual observation showed good inhibition against *Rhizopus* and *Botrytis* growth similar to the results in example (F).

(I) The microcapsules prepared according to Example 7A were tested on peppers as described in Example 1E against *Rhizopus* and *Botrytis*. The results obtained by visual observation showed good inhibition against *Rhizopus* and *Botrytis* growth similar to the results in example (F).

(J) The microcapsules prepared according to Example 8A were tested on peppers as described in Example 1E against *Rhizopus* and *Botrytis*.

Tests were carried out to observe development of fungi (*Rhizopus* and *Botrytis*) on the stems of peppers treated by formulations 10-ETBW and 12-ETSt, over a period of 35 days.

The results show that in the first 21 days no fungi have grown (even in the control group). The peppers treated by the 12-ETSt formulation (microcapsules coated with stearic acid) have started rotting after 28 days, with a slow rotting rate. The peppers treated by the 10-ETBW (microcapsules with a Bees wax coating) started rotting earlier at 21 days (10% infection), but after 28 days the rate of rotting was slower than with 12-ETSt. At 35 days peppers from both groups both had a 13% infection. The control at 28 and 35 days had a 17% and 30% infection.

A summary of the efficacy of various treatments on the development of fungi (*Rhizopus* and *Botrytis*) on the stem of the peppers, over a period of 35 days, as the percentage of undamaged pepper stings is as follows: The % of non-infected peppers was 90 to 95% for 2ETW, 85% for 10 ETBW, and 12-ETSt, 80% for and 80% for 3-ETW and 58% for the control.

It appears that the 2-ETW formulation, containing 50% oregano oil and 50% tea tree oil, was the most effective after 35 days.

Oil Release Rate Results

The release rate of various formulations differing in the active ingredient and in the coating thickness was studied. The different formulation 2, 7 and 8 ETW compositions are given in the Table below. The coating thickness in % is meant to compare the thinnest coating (designated 100%) with coating that use more material which in the case of 200% means twice the coating thickness as inferred from the use of 200% more coating material.

| | Active Ingredient | | Coating Thickness |
|---|---|---|---|
| Sample | Tea tree oil | Oregano oil | (paraffin wax) (%) |
| 2-ETW | 50 | 50 | 100% |
| 8-ETW | 80 | 20 | 200% |
| 7-ETW | 20 | 80 | 200% |

In the rates of release experiments the first measurement was taken at time zero (when the active ingredients were incorporated into the capsule), at which time the percentage of active ingredient is normalized to 100%.

The next measurements were taken on a weekly basis, for 6 weeks.

All the tested formulations released the oil in a similar manner. After 3 weeks the amount retained in 2, 7 and 8-ETW are 62%, 70% and 48% respectively. In the 2-ETW formulation, even after 6 weeks, the percentage of active ingredient was over 30% of the initial amount, while for 8 ETW and 7 ETW it was 2% and 15% respectively.

In comparing the release rate the release rate of various formulations containing pure oregano oil, and differing in the coating material (see Table below for different coatings), all in a maximum coating thickness of 200% as compared to the thinnest outer coated microcapsules (see above explanation of the meaning of % in film thickness) the following results were observed. Formulation 12-ETSt had a 30% of the oil remaining after 6 weeks and 10 ETBW and % ETW had 25% and 19% respectively:

| Sample | Coating |
|---|---|
| 12-ETSt | Stearic acid |
| 10-ETBW | Bee's wax |
| 5-ETW | Paraffin Oil |

The release rates of formulations 13-ETSt and 16-ETSt, both having a combination of oregano oil and cotton seed oil (10%) and coated by stearic acid where studied. Formulation 13-ETSt has a 400% coating thickness versus 200% in the 16-ETSt sample prepared in example 9A (see above explanation of the meaning of % in film thickness). In addition microcapsules of 16-ETSt sample was prepared by double interfacial polymerization. In both formulations after 1, 3 and 6 weeks the amount of essential oil remaining in the microcapsuale wa 95-98%, 80% and 70% respectively It appears that either doubling the polyurea coating or increasing the wax thickness to 400% achieved a similar release rate and a higher oil retentions (in effect lower release rate) as compared to the previously described microcapsules. Thus by the approaches described such as the inclusion of cotton seed oil, and the use of multiple coating vs single or multiple IP layers the essential oil release rates of the claimed powders can be controlled and optimized for a given application.

Example Test 2: Veterinary Application of Solid Core Microcapsules

Solid microcapsules containing Citronella oil and Pyrethrum prepared according to Example 1A experiments, wherein the formulation for citronella was used in the same weight as the tea tree oil of example 1A and the pyrethrum was added to be 10% of the amount of citronella. This was mixed in a ratio of 5-15% by weight with each of the following plastics: P.V.C, Polypropylene and Polyethylene, up to 95% plastic and no more than 15% microcapsules. Each time, the mixture was melted and extruded from an extruder at the minimum temperatures needed to achieve plastic flow into animal collar molds.

Efficacy against flies, fleas and ticks was checked by visual observation on dogs, horses and cows and the results were very promising. The results showed a significant reduction of infection compared to the control.

Example Test 3: Environmental Application of Solid Core Microcapsules

Solid microcapsules containing Citronella and Pyrethrum in a ratio of 10/1 by weight, or: Qwenling and Pyrethrum also in a ration of 10/1 by weight were prepared according to example 1A wherein the formulation for citronella was used in the same weight as the tea tree oil of example 1A and the pyrethrum was added to be 10% of the amount of citronella. Similarly Qwenling formulations were prepared according to example 1A wherein the formulation for Qwenling was used in the same weight as the tea tree oil of example 1A and the pyrethrum was added to be 10% of the amount of Qwenling.

These powders were mixed with low-density polyethylene in a ratio of (but not limited to) 90/10 polymer to essential oil and then melted and extruded into table cloth mold. The obtained plastic tablecloth, containing microcapsules incorporated therein, were checked visually for their efficacy against flies and mosquitoes in balconies, gardens and event gardens and the results were very good. In effect they were very effective in repelling both flies and mosquitoes.

Example Test 4: Water Treatment Application of Solid Core Microcapsules

The following solid microcapsules were prepared and tested against *Chironomus* larvae and eggs, as well as on copepods (small crustaceans).

General Methods:

In the following experiments, the tested formulations were diluted varying ratios: 1:100,000, 1:200,000, 1:500, 000 etc.

Determining Survival Rates of *Chironomus* Larvae

The experiments were conducted on *Chironomus* larvae up to 1 day post hatching.

A bioassay experiment was conducted in 20 cc scintillation test tubes. The test tubes were filled with 10 ml of either tap water (in the control samples) or the microcapsular formulation suspended in tap water. 10-20 larvae were then put in each test tube.

In the first two experiments, the survival rate was determined by checking larvae movement in the water. In the third experiment, the survival rate was determined by counting the live and dead bacteria in the different test tubes, 24 hours and 48 hours after incubation.

Each formulation was tested in 3 repetitions (a total of 12 samples and 5 control samples.

Determining Hatching Rates of *Chironomus* Eggs

The test tubes contained 10 ml of either tap water (in the control samples) or a microcapsular formulation suspended in tap water. One freshly collected egg batch was put in each test tubes. Determination of hatching rate was determined by checking the hatching and looking under a binocular whether the hatched larvae are alive or dead.

Determining Survival Rates of Copepods

The test tubes were filled with 2 ml of either tap water (in the control samples) or the microcapsular formulation suspended in tap water. 1 freshly collected copepod was then put in each test tube. In another set of experiments, the copepod that was used had been collected 24 hours earlier.

The survival rate was determined by checking larvae movement in the water. In the third experiment, the survival rate was determined by looking under a binocular whether the copepods were alive or dead, 24 hours and 48 hours after incubation.

Each formulation was tested in 6 repetitions (a total of 24 samples and 12 control samples.

Water Application Results

A) Survival Rates of *Chironomus* Larvae
I. Experiment L1

| 24 hours | 12 hours | Dilution ratio | Formulation No. |
|---|---|---|---|
| no movement | movement | 1:100,000 | #W1 |
| no movement | movement | 1:200,000 | |
| no movement | movement | 1:500,000 | |
| no movement | movement | 1:100,000 | #W2 |
| no movement | movement | 1:200,000 | |
| no movement | movement | 1:500,000 | |
| no movement | movement | 1:100,000 | #W3 |
| no movement | movement | 1:200,000 | |
| no movement | movement | 1:500,000 | |
| no movement | movement | 1:100,000 | #W4 |
| no movement | movement | 1:200,000 | |
| no movement | movement | 1:500,000 | |
| All larvae are alive | All larvae are alive | 0 | Tap water (control) |

II. Experiment L2

| 24 hours | 12 hours | Dilution ratio | Formulation No. |
|---|---|---|---|
| no movement | no movement | 1:5,00 | #W1 |
| no movement | no movement | 1:10,000 | |
| no movement | no movement | 1:50,000 | |
| no movement | no movement | 1:5,00 | #W2 |
| no movement | no movement | 1:10,000 | |
| no movement | no movement | 1:50,000 | |
| no movement | no movement | 1:5,00 | #W3 |
| no movement | no movement | 1:10,000 | |
| no movement | no movement | 1:50,000 | |
| no movement | no movement | 1:5,00 | 4# |
| no movement | no movement | 1:10,000 | |
| no movement | no movement | 1:50,000 | |
| All larvae are alive | All larvae are alive | 0 | Tap water (control) |

III. Experiment L3

| 24 hours | Dilution ratio | Formulation No. |
|---|---|---|
| no movement | 1:50,000 | #W1 |
| no movement | 1:100,000 | |
| no movement | 1:200,000 | |
| no movement | 1:400,000 | |
| no movement | 1:50,000 | #W2 |
| no movement | 1:100,000 | |
| no movement | 1:200,000 | |
| no movement | 1:400,000 | |
| no movement | 1:50,000 | #W3 |
| no movement | 1:100,000 | |
| no movement | 1:200,000 | |
| no movement | 1:400,000 | |
| no movement | 1:50,000 | 4# |
| no movement | 1:100,000 | |
| no movement | 1:200,000 | |
| no movement | 1:400,000 | |
| 6/8, 10/12, 8/12 Number of live larvae of the initial number | 0 | Tap water (control) |

B) Hatching Rates of *Chironomus* Eggs
I. Experiment T1

| 48 hours | 24 hours | Dilution ratio | Formulation No. |
|---|---|---|---|
| 0/5 | 0/5 | 1:5,000 | #W1 |
| 0/5 | 0/5 | 1:10,000 | |
| 3/5 | 0/5 | 1:50,000 | |
| 0/5 | 0/5 | 1:5,000 | #W2 |
| 0/5 | 0/5 | 1:10,000 | |
| 2/5 | 0/5 | 1:50,000 | |
| 0/5 | 0/5 | 1:5,000 | #W3 |
| 0/5 | 0/5 | 1:10,000 | |
| 4/5 | 0/5 | 1:50,000 | |
| 0/5 | 0/5 | 1:5,000 | #W4 |
| 0/5 | 0/5 | 1:10,000 | |
| 3/5 | 0/5 | 1:50,000 | |
| 5/5 | 3/5 | 0 | Tap water (control) |

Numbers indicate hatched bathes of the total number of batches.

II. Experiment L2

| 72 hours | 48 hours | 24 hours | Dilution ratio | Formulation No. |
|---|---|---|---|---|
| 0/5 | 0/5 | 0/5 | 1:10,000 | #W1 |
| 0/5 | 0/5 | 0/5 | 1:20,000 | |
| 0/5 | 0/5 | 0/5 | 1:40,000 | |
| 0/5 | 0/5 | 0/5 | 1:10,000 | #W2 |
| 0/5 | 0/5 | 0/5 | 1:20,000 | |
| 0/5 | 0/5 | 0/5 | 1:40,000 | |
| 0/5 | 0/5 | 0/5 | 1:10,000 | #W3 |
| 4/5 | 0/5 | 0/5 | 1:20,000 | |
| 5/5 | 0/5 | 0/5 | 1:40,000 | |
| 0/5 | 0/5 | 0/5 | 1:10,000 | #W4 |
| 5/5 | 1/5 | 0/5 | 1:20,000 | |
| 5/5 | 2/5 | 0/5 | 1:40,000 | |
| 5/5 | 5/5 | 3/5 | 0 | Tap water (control) |

III. Experiment T3

| 72 hours | 48 hours | 24 hours | Dilution ratio | Formulation No. |
|---|---|---|---|---|
| 1/3 | 1/3 | 0/3 | 1:10,000 | Placebo (empty capsules) |
| 1/3 | 1/3 | 0/3 | 1:20,000 | |
| 1/3 | 0/3 | 0/3 | 1:40,000 | |
| 1/3 | 1/3 | 0/3 | 1:100,000 | |
| 0/3 | 0/3 | 0/3 | 1:10,000 | #W1 |
| 0/3 | 0/3 | 0/3 | 1:20,000 | |
| 0/3 | 0/3 | 0/3 | 1:40,000 | |
| 1/3 | 1/3 | 0/3 | 1:100,000 | |

-continued

| 72 hours | 48 hours | 24 hours | Dilution ratio | Formulation No. |
|---|---|---|---|---|
| 0/3 | 0/3 | 0/3 | 1:10,000 | #W2 |
| 0/3 | 0/3 | 0/3 | 1:20,000 | |
| 0/3 | 0/3 | 0/3 | 1:40,000 | |
| 0/3 | 0/3 | 0/3 | 1:100,000 | |
| 0/3 | 0/3 | 0/3 | 1:10,000 | #W3 |
| 1/3 | 1/3 | 0/3 | 1:20,000 | |
| 0/3 | 0/3 | 0/3 | 1:40,000 | |
| 0/3 | 0/3 | 0/3 | 1:100,000 | |
| 0/3 | 0/3 | 0/3 | 1:10,000 | #W4 |
| 1/3 | 1/3 | 0/3 | 1:20,000 | |
| 0/3 | 0/3 | 0/3 | 1:40,000 | |
| 2/3 | 2/3 | 0/3 | 1:100,000 | |
| 1/4 | 1/4 | 0/4 | 0 | Tap water (control) |

C) Copepods' Survival Rates Experiments

I. Experiment K1

| 24 hours | Dilution ratio | Formulation No. |
|---|---|---|
| 6/6 | 1:1,000 | Placebo (empty capsules) |
| 6/6 | 1:5,000 | |
| 6/6 | 1:10,000 | |
| 6/6 | 1:50,000 | |
| 0/6 | 1:1,000 | #W1 |
| 0/6 | 1:5,000 | |
| 0/6 | 1:10,000 | |
| 0/6 | 1:50,000 | |
| 0/6 | 1:1,000 | #W2 |
| 0/6 | 1:5,000 | |
| 0/6 | 1:10,000 | |
| 0/6 | 1:50,000 | |
| 0/6 | 1:1,000 | #W3 |
| 0/6 | 1:5,000 | |
| 0/6 | 1:10,000 | |
| 0/6 | 1:50,000 | |
| 0/6 | 1:1,000 | #W4 |
| 0/6 | 1:5,000 | |
| 0/6 | 1:10,000 | |
| 0/6 | 1:50,000 | |
| 10/12 | 0 | Tap water (control) |

The numbers indicate the number of live Copepods of the initial number of Copepods.

II. Experiment K2

| 24 hours | Dilution ratio | Formulation No. |
|---|---|---|
| 3/3 | 1:100,000 | Placebo (empty capsules) |
| 3/3 | 1:500,000 | |
| 0/6 | 1:100,000 | #W1 |
| 5/6 | 1:500,000 | |
| 0/6 | 1:100,000 | #W2 |
| 5/6 | 1:500,000 | |
| *1/6 | 1:100,000 | #W3 |
| 5/6 | 1:500,000 | |
| *1/6 | 1:100,000 | #W4 |
| 4/6 | 1:500,000 | |
| 10/12 | 0 | Tap water (control) |

The numbers indicate the number of live Copepods of the initial number of Copepods.
*the 1 live copepod appeared to be dying.

The invention claimed is:

1. A microcapsule comprising:
a solid core having at least one essential oil in a mixture with a porous solid material;
at least one film layer uniformly encapsulating the solid core, the at least one encapsulating film layer including a) a polyurea film and/or a polyurethane film, or b) an amphipathic shell composed of a multivalent salt form of at least one alkanoic acid; and
at least one fatty layer formed around the encapsulating film layer,
wherein the at least one fatty layer and the at least one film layer control the release rate of the at least one essential oil from the solid core, such that the thickness of the at least one fatty layer at least partially controls the release rate of said essential oil, and such that the at least one fatty layer and the at least one film layer have a combined effect on the release rate of said essential oil.

2. The microcapsule of claim 1, wherein the porous solid material is an aerogel.

3. The microcapsule of claim 2, wherein the aerogel comprises silica, carbon aerogel, alumina aerogel, chalcogel or any combination thereof.

4. The microcapsule of claim 1, wherein the fatty layer comprises a fatty material selected from the group consisting of a wax, a fat, a fatty acid, a lipid, and a low-melting polymer.

5. The microcapsule of claim 1, wherein the microcapsule has an average size of from 0.1 to 1000 microns.

6. A composition comprising a plurality of the microcapsules of claim 1, and at least one carrier, additive, adjuvant or additional active ingredient.

7. A method for preventing and/or treating insect infestation, bacterial infections and/or fungal infections in harvested crops and/or in products prone to develop such infections, the method comprising exposing the crops or the products to the microcapsules of claim 1, or to a composition comprising the microcapsules of claim 1 and at least one of a carrier, an additive, an adjuvant, and an additional active ingredient.

8. The method of claim 7, wherein the microcapsules or the composition are contained in a closed sachet, thereby preventing any direct contact between the crops and/or products and the microcapsules.

9. A method for repelling pests in an environment, the method comprising incorporating the microcapsules of claim 1, or a composition comprising the microcapsules of claim 1 and at least one of a carrier, an additive, an adjuvant, and an additional active ingredient, in plastic household products or in plastic outdoor products.

10. The microcapsule of claim 1, further comprising an insect growth regulator (IGR) selected from the group consisting of Neem oil, components of Neem oil, Azadirachtin, synthetic components of Neem oil, Pyriproxyfen, and any combination thereof.

11. The microcapsule of claim 5, wherein the microcapsule has an average size of from 10 to 100 microns.

12. The microcapsule of claim 1, wherein the at least one film layer comprises at least two film layers formed around the solid core.

13. The microcapsule of claim 1, wherein the at least one fatty layer comprises at least two fatty layers formed around the film layer.

14. The microcapsule of claim 1, wherein the density of the microcapsules is at or above 1 kg/m$^3$.

15. The microcapsule of claim 1, wherein the film layer comprises a polyurethane film.

16. The microcapsule of claim 1, wherein said core further comprises at least one plant oil adapted to control the release rate of said essential oil.

17. The microcapsule of claim 1, wherein the at least one essential oil is 29-64% w/w of the microcapsule.

18. The microcapsule of claim 1, wherein 95% to 98% of the at least one essential oil is retained in the microcapsule for 1 week after application to a substrate.

19. The microcapsule of claim 1, wherein the microcapsules are contained in a closed sachet.

20. The microcapsule of claim 1, wherein the at least one film layer has a thickness of between about 0.5 nanometer to about 10 microns.

21. The microcapsule of claim 1, wherein the release rate of the at least one essential oil is a zero order release rate.

22. The microcapsule of claim 1, wherein the at least one film layer controls the release rate of the at least one essential oil from the solid core.

23. The microcapsule of claim 1, wherein the at least one film layer is prepared by interfacial polymerization or complexation.

24. The microcapsule of claim 1, wherein the at least one film layer is prepared by double interfacial polymerization.

25. The microcapsule of claim 1, wherein the at least one film layer has a thickness of between about 0.5 nanometer to about 10 microns.

* * * * *